United States Patent [19]

James et al.

[11] Patent Number: 5,086,051

[45] Date of Patent: Feb. 4, 1992

[54] 1H, 3H-PYRROLO[1,2-C]THIAZOLE-7-CARBOX-AMIDE DERIVATIVES AND PHARMACEUTICAL COMPOSITIONS CONTAINING THEM

[75] Inventors: Claude James; Daniel Lave; Francoise Soler, all of Paris, France

[73] Assignee: Rhone-Poulenc Sante, Antony Cedex, France

[21] Appl. No.: 493,439

[22] Filed: Mar. 14, 1990

[30] Foreign Application Priority Data

Mar. 17, 1989 [FR] France ................... 8903510

[51] Int. Cl.$^5$ ................ C07D 513/04; C07D 417/04; A61K 31/425
[52] U.S. Cl. ........................... 514/228.2; 514/233.2; 514/253; 514/305; 514/309; 514/310; 514/318; 514/312; 514/313; 514/314; 514/333; 514/338; 544/58.6; 544/121; 544/127; 544/128; 544/362; 544/363; 544/364; 544/129; 544/131; 546/133; 546/135; 546/137; 546/147
[58] Field of Search ............. 546/194, 133, 157, 159, 546/174, 175, 145, 256, 270; 514/318, 228.2, 233.2, 253, 305, 333, 338; 544/58.6, 128, 364, 131, 135

[56] References Cited

U.S. PATENT DOCUMENTS 4,529,728 7/1985 Fabre et al. ................. 514/227
4,786,645 11/1988 Fabre et al. ................. 514/333

Primary Examiner—Joseph Paul Brust
Assistant Examiner—M. S. H. Gabilan
Attorney, Agent, or Firm—Morgan & Finnegan

[57] ABSTRACT

New derivatives of formula (I) in which $R_1$=H, halogen, alkyl, alkyloxy, $CF_3$, $NH_2$, alkylamino, dialkylamino, OH, CH, phenyl or phenoxy, Ar=phenyl, naphthyl, pyridyl, quinolyl, isoquinolyl, thienyl, thieno[2,3-b]thienyl or thieno[3,2-b]thienyl (these groups optionally substituted with halogen, alkyl, alkyloxy, $CF_3$, $NH_2$, alkylamino, dialkylamino, OH or CN), p=0, 1 or 2, and A—either Z=valency bond and $R_2$=H B—or Z=valency bond and $R_2$=pyridyl, quinuclidinyl, 3-pyrrolidinyl, 3- or 4-piperidyl (these groups optionally being substituted with alkyl, hydroxyalkyl, phenyl or phenylalkyl)

C—or Z=alkylene radical (1 to 4C) and $R_2$=2-, 3- or 4-pyridyl, 3-quinuclidinyl, 2- or 3-pyrrolidinyl, 2-, 3- or 4-piperidyl (optionally substituted with alkyl, hydroxyalkyl, phenyl or phenylalkyl) or $R_2$=CON($R_3$)($R_4$) where a) either $R_3$ and $R_4$ form a piperazine optionally substituted with alkyl, hydroxyalkyl, pyridyl, phenyl or phenylalkyl, b) or $R_3$=H, alkyl, phenyl or phenylalkyl, or $(CH_2)_nN(R_5)$ ($R_6$) where $1<n<4$ and $R_5$ and $R_6$=H, alkyl, phenyl, phenylalkyl, or $R_5$ and $R_6$ form a morpholine, thiomorpholine, pyrrolidine, piperidine or piperazine ring, (optionally substituted with alkyl, hydroxyalkyl, pyridyl, phenyl, phenylalkyl or phenylcarbonyl), and $R_4=(CH_2)_nN(R_5)(R_6)$ defined as above, D- or Z=alkylene (1 to 4C) and $R_2$=N($R_3$) ($R_4$) or N($R_5$)$R_6$) where $R_3$, $R_4$, $R_5$ and $R_6$ are defined as above in C b), on the understanding that the alkyls contain 1 to 4C in a straight or branched chain and that the invention relates to the racemates, the enantiomers and mixtures thereof, the diastereoisomers, pure or mixed, and the E and Z isomers, as well as to the salts of these products.

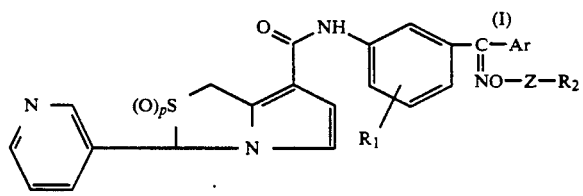

2 Claims, No Drawings

1H, 3H-PYRROLO[1,2-C]THIAZOLE-7-CARBOXAMIDE DERIVATIVES AND PHARMACEUTICAL COMPOSITIONS CONTAINING THEM

The present invention relates to new 1H,3H-pyrrolo[1,2-c]thiazole-7-carboxamide derivatives of general formula:

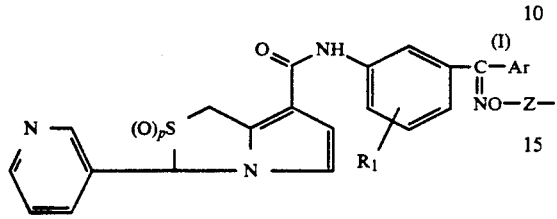

in which $R_1$ represents a hydrogen or halogen atom or an alkyl, alkyloxy, trifluoromethyl, amino, alkylamino, dialkylamino, hydroxy, cyano, phenyl or phenoxy radical, Ar represents a phenyl, naphthyl, pyridyl, quinolyl, isoquinolyl, thienyl, thieno[2,3-b]thien-2-yl or thieno[3,2-b]thien-2-yl, it being possible for these radicals optionally to bear one or more substituents selected from halogen atoms or alkyl, alkyloxy, trifluoromethyl, amino, alkylamino, dialkylamino, hydroxy or cyano radicals, p represents an integer equal to zero, one or two, and A— either Z represents a valency bond and $R_2$ represents a hydrogen atom, B— or Z represents a valency bond and $R_2$ represents a 2- or 4-pyridyl, 3-quinuclidinyl, 3-pyrrolidinyl or 3- or 4-piperidyl radical, it being possible for the latter two radicals to be optionally substituted on the nitrogen atom with an alkyl, hydroxyalkyl, phenyl or phenylalkyl radical, C— or Z represents an alkylene radical containing 1 to 4 carbon atoms and $R_2$ represents a 2-, 3- or 4-pyridyl, 3-quinuclidinyl, 2- or 3-pyrrolidinyl or 2-, 3- or 4-piperidyl radical, it being possible for the latter two radicals to be substituted on the nitrogen atom with an alkyl, hydroxyalkyl, phenyl or phenylalkyl radical, or alternatively $R_2$ represents a radical of general formula:

in which:

a) either $R_3$ and $R_4$, together with the nitrogen atom to which they are attached, form a piperazine ring optionally substituted on the second nitrogen atom with an alkyl, hydroxyalkyl, pyridyl, phenyl or phenylalkyl radical, b) or $R_3$ represents a hydrogen atom or an alkyl, phenyl or phenylalkyl radical or a radical of general formula:

in which n represents an integer between 1 and 4 and $R_5$ and $R_6$, which may be identical or different, represent a hydrogen atom or an alkyl, phenyl or phenylalkyl radical, or alternatively $R_5$ and $R_6$, together with the nitrogen atom to which they are attached, form a morpholine, thiomorpholine, pyrrolidine, piperidine or piperazine ring in which the second nitrogen atom can be optionally substituted with an alkyl, hydroxyalkyl, pyridyl, phenyl, phenylalkyl or phenylcarbonyl radical, and $R_4$ represents a radical of general formula (III) defined as above, on the understanding that the definitions of n, $R_5$ and $R_6$ in the symbols $R_3$ and $R_4$ can be identical or different, D— or Z represents an alkylene radical containing 1 to 4 carbon atoms and $R_3$ represents a radical of general formula:

or

in which $R_3$, $R_4$, $R_5$ and $R_6$ are defined as above in C a) and b), on the understanding that the alkyl radicals and alkyl portions contain 1 to 4 carbon atoms in a straight or branched chain and that the invention relates to the racemic products, the enantiomers due to the presence of an asymmetric carbon at the 3-position of the pyrrolothiazole ring, the mixtures of these enantiomers, the diastereoisomers, pure or mixed, due to the possible presence of another chiral centre, and the E and Z (also known as syn and anti) isomers and mixtures thereof originating from the presence of the oxime group C=NO-Z-$R_2$, as well as to the pharmaceutically acceptable salts of the products of formula (I) thus defined.

According to the invention, the products of general formula (I) may be prepared by the action of a hydroxylamine of general formula:

in which Z and $R_2$ are defined as above, on a ketone of general formula:

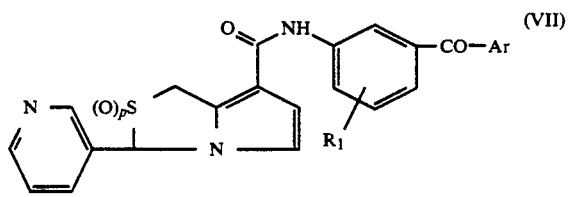

in which the symbols p, R and Ar are defined as above.

In practice, the hydroxylamine of general formula (VI) is used in the form of a hydrochloride, and the reaction is performed in an organic solvent such as pyridine or a low molecular weight alcohol such as propanol in the presence of an acceptor for acids such as an alkali metal carbonate at a temperature between 20°

C. and the refluxing temperature of the reaction mixture.

The products of general formula (VI) may be prepared by application or adaptation of methods described in the literature.

The products of general formula (VII) in which p is equal to 1 or 2 may be obtained by oxidation of a product of general formula (VII) in which p is equal to 0, that is to say a product of general formula:

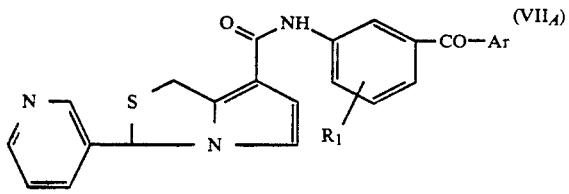
(VII$_A$)

in which R$_1$ and Ar are defined as above.

The oxidation may be carried out, e.g., by employing an agent commonly used for converting a sulphide to a sulphoxide or a sulphone, working in a suitable solvent. For example, it is possible to employ hydrogen peroxide in acetone or acetic acid, an alkali metal periodate in an alcohol or acetonitrile, or a percarboxylic acid (peracetic, perbenzoic, m-chloroperbenzoic, p-nitroperbenzoic or perphthalic acid) in an ether (dioxane, tetrahydrofuran, diethyl ether), a chlorinated solvent (dichloromethane, 1,2-dichloroethane), acetic acid or a mixture of these solvents. The reaction is generally performed at a temperature of between −10° C. and +20° C.

It is especially advantageous to work in dichloromethane in the presence of m-chloroperbenzoic acid, at a temperature of between 0° and 20° C.

When it is desired to obtain the sulphoxide, it is necessary to perform the reaction with one equivalent of oxidizing agent. When it is desired to obtain the sulphone, it is necessary to use at least two equivalent of oxidizing agent. The actual oxidation reaction is performed in the presence of at least one equivalent of acid such as methanesulphonic acid, at a temperature in the region of 20° C.

The products of general formula (VII) in which p is equal to zero, i.e. the products of general formula (VII$_A$) may be prepared according to the method described in the European Patent Application published under No. 0,253,711.

According to the invention, the products of general formula (I) in which the symbols are defined as above in B, C or D may be prepared by the action of a product of general formula:

X-Z-R$_2$ (VIII)

in which Z and R$_2$ are defined as above and X represents a halogen atom such as a chlorine, bromine or iodine atom, or a reactive ester residue such as mesyloxy or tosyloxy, on a product of general formula (I) defined as above in A, i.e. a product of general formula:

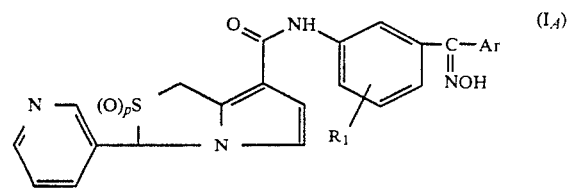
(I$_A$)

in which p, R$_1$ and Ar are defined as above.

The reaction is generally performed in an organic solvent such as dimethylformamide at a temperature in the region of 20° C. in the presence of a condensing agent such as an alkali metal hydride, e.g. sodium hydride, or in a low molecular weight alcohol such as ethanol or t-butanol in the presence of an alkali metal alcoholate such as sodium ethylate or potassium t-butylate under reflux.

The products of general formula (I$_A$) may be prepared by the action of a product of general formula (VI) in which Z represents a valency bond and R$_2$ represents a hydrogen atom on a product of general formula (VII), as stated above.

The products of general formula (I$_A$) in which p is equal to 1 or 2 may also be prepared by oxidation of a product of general formula (I) in which p is equal to zero and R and Ar are defined as above in A, that is to say a product of general formula:

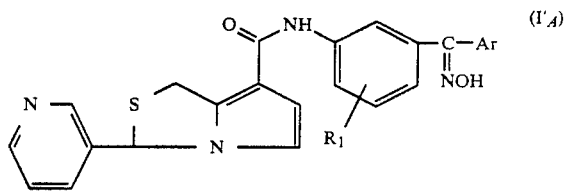
(I'$_A$)

The oxidation may be carried out as stated above for the oxidation of a product of general formula (VII$_A$).

According to the invention, the products of general formula (I) in which p is equal to 0 may also be obtained by the action of a 7-chloroformyl-3-(3-pyridyl)-1H,3H-pyrrolo[1,2-c]thiazole derivative of general formula:

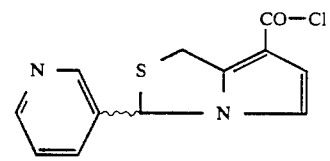
(IX)

in R or S form or mixtures thereof, on an oxime of general formula:

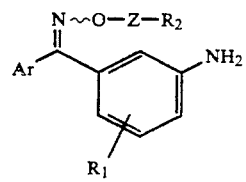
(X)

in which Ar, Z, R$_1$ and R$_2$ are defined as above, in E or Z form or mixtures thereof.

In general, the condensation is performed under the usual conditions for preparing amides by the action of an acid chloride on a primary amine.

The product of general formula (X) may be obtained by the action of a product of general formula (VIII) on an oxime of general formula:

in which Ar and $R_1$ are defined as above, in E or Z form or in mixtures thereof.

In general, the reaction is performed in the presence of an alkali metal hydride such as sodium hydride, working in an organic solvent such as dimethylformamide at a temperature in the region of 20° C.

The oxime of general formula (XI), in E or Z form, may be obtained by separation, e.g. by chromatography, of a mixture of E and Z forms.

The mixture of E and Z forms of the oxime of general formula (XI) may be obtained by the action of a hydroxylamine salt (hydrochloride, tosylate) on a product of general formula:

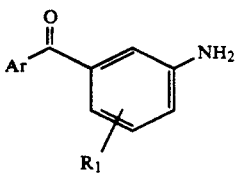

in which Ar and $R_1$ are as defined above.

In general, the reaction is performed in an organic solvent such as pyridine or a low molecular weight alcohol such as propanol in the presence of an acceptor for acid such as an alkali metal carbonate, e.g. sodium carbonate, at a temperature between 20° C. and the boiling point of the reaction mixture.

The product of general formula (X) may also be obtained by the action of a hydroxylamine of general formula (VI) on a ketone of general formula (XII) under the conditions described above for the action of a hydroxylamine of general formula (VI) on a ketone of general formula (VII).

The products of general formula (I) in which p is equal to 1 may be obtained by oxidation of a product of general formula (I) in which p is equal to 0.

In general, the oxidation is accomplished by means of an oxidizing agent such as hydrogen peroxide or m-chloroperbenzoic acid. It is especially advantageous to use hydrogen peroxide.

When, in the present invention, a particular product is referred to by its chemical name, it is understood that, in the absence of special indications, the racemic product or the mixture of syn and anti isomers is always referred to.

The products of general formula (I) in which the substituents Ar and 0-Z-$R_2$ of the oxime group are in the syn or anti (E o Z) position may be prepared from the corresponding mixtures by conventional classical methods such as high performance liquid chromatography (HPLC).

The products of general formula (I) ca exist in racemic form or in the form of pure enantiomers due to the fact that the carbon atom at the 3-position of the pyrrolothiazole ring is asymmetric. To obtain the products of general formula (I) in the state of pure enantiomers, it is advantageous to employ the processes described above using an already resolved product of general formula (VII); the latter may be prepared according to the method described in the European Patent Application published under No. 0,253,711.

For those skilled in the art, it is understood that, to carry out the processes described above, it may be necessary to introduce protective groups on some groups present in the radicals Ar, R and $R_6$ of the different products employed. The protective group may then be removed at the most opportune point of the synthesis. Thus, when an amino or alkylamino group is present in the radical Ar, $R_1$ and/or $R_2$, this group may be protected, e.g. with a t-butyloxycarbonyl radical and then liberated after the reaction by means of an aqueous acid, e.g. by means of aqueous hydrochloric acid solution or, preferably, by means of an acetic acid solution of hydrogen chloride gas. When a hydroxy group is present in the radical Ar, $R_1$ and/or $R_2$, this group may be advantageously protected in the form of a tetrahydropyranyloxy or methoxymethyloxy radical, and then liberated after the reaction by hydrolysis.

The new products of general formula (I) may be purified by the usual known methods, e.g. by crystallization or by chromatography.

The new products of general formula (I) may be converted to addition salts with acids by reaction with an acid in an organic solvent such as an alcohol, a ketone, an ether or a chlorinated solvent. The salt precipitates, where appropriate after concentration of its solution; it is separated by filtration or decantation.

The new products according to the invention, as well as their pharmaceutically acceptable salts, display advantageous properties combined with low toxicity. They are generally active at concentrations below 0.5 nM in the test of measurement of inhibitory activity in vitro with respect to platelet aggregation induced by 1-0-octadecyl-2-acetyl-sn-glyceryl-3-phosphorylcholine (PAF-acether), according to the technique of G. V. R. BORN et al., J. Physiol., 168, 178 (1963).

Their toxic dose (expressed as the $LD_{50}$) in mice is generally between 300 and 900 mg/kg when administered orally.

For therapeutic use, the new products of formula (I) may be employed as they are or, where appropriate, in the state of pharmaceutically acceptable salts, i.e. salts which are non-toxic at the doses at which they are used.

As pharmaceutically acceptable salts, there may be mentioned the addition salts with inorganic acids, such as hydrochlorides, sulphates, nitrates or phosphates, or organic acids, such as acetates, propionates, succinates, benzoates, fumarates, maleates, methanesulphonates, isethionates, theophyllineacetates, salicylates, phenolphthalinates, methylenebis($\beta$-hydroxynaphthoates) or substitution derivatives of these compounds.

The examples which follow, given without implied limitation, show how the invention may be put into practice.

EXAMPLE 1

Sodium carbonate (5.30 g) and hydroxylamine hydrochloride (6.95 g) are added to a suspension of (+)-N-(3-benzoylphenyl)-3-(3-pyridyl)-1H,3H-pyrrolo[1,2- c]thiazole-7-carboxamide (21.27 g) in 1-propanol (250 cc). The suspension is heated to reflux with stirring for 2 hours. The solvent is evaporated off under reduced pressure (20 mm Hg; 2.7 kPa) at a temperature in the region of 45° C. The residue is taken up in distilled water (250 cc) and crystallization is primed. The crystals which appear are separated by filtration, washed 4 times with distilled water (300 cc in total) and then dried in the air. A product (22.04 g), m.p. 210° C., is thereby obtained. 2 g of this product are dissolved in boiling 1-propanol (80 cc). The solution obtained is filtered while hot and the filtrate is cooled to a temperature in the region of 0° C. for 48 hours. The crystals which appear are separated by filtration, washed three times with absolute ethanol (10 cc in total) and then dried under reduced pressure (0.1 mm Hg; 13.5 Pa) at a temperature in the region of 60° C. (+)-N-[3-(α-Hydroxyiminobenzyl)phenyl]-3-(3-pyridyl)-1H,3H-pyrrolo[1,2-c]thiazole-7-carboxamide (mixture of E and Z forms) (1.74 g) is thereby obtained in the form of white crystals, m.p. 151°–155° C.

(+)-N-(3-Benzoylphenyl)-3-(3-pyridyl)-1H,3H-pyrrolo[1,2-c]thiazole-7-carboxamide is prepared according to the method described in the European Patent Application published under No. 0,253,711.

EXAMPLE 2

A solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (2 g) in anhydrous N,N-dimethylformamide (10 cc) is added under a stream of nitrogen in the course of approximately 5 minutes to a mixture of a 50% strength dispersion (325 mg) of sodium hydride in liquid paraffin and anhydrous N,N-dimethylformamide (4 cc). After stirring for a quarter of an hour at room temperature, a solution of 1-(3-chloropropyl)-4-phenylpiperazin (1.19 g) in N,N-dimethylformamide (3 cc) is added in the course of approximately 2 minutes, and the solution obtained is stirred for 16 hours at room temperature. Distilled water (150 cc) is then added and crystallization is primed. After 3 hours' stirring at room temperature, the crystals obtained are separated by filtration, washed 3 times with distilled water (45 cc in total) and dried under reduced pressure (0.1 mm Hg; 13.5 Pa) at a temperature in the region of 20° C. A product (2.74 g) is thereby obtained. This product is dissolved in acetone (15 cc). The solution obtained is treated with oxalic acid (0.77 g) and stirred for 3 hours at room temperature. The crystals obtained are separated by filtration, washed 4 times with acetone (20 cc in total) and dried under reduced pressure (0.1 mm Hg; 13.5 Pa) at a temperature in the region of 60° C. (+)-N-[3-{α-[3-(4-Phenyl-1-piperazinyl)propoxyimino]benzyl}phenyl.-3-(3-pyridyl)-1H,3H-pyrrolo[1,2-c]thiazole-7-carboxamide acid dioxalate (mixture of E and Z forms) (2.74 g) is thereby obtained in the form of cream-coloured crystals, m.p. 130° C.

1-(3-Chloropropyl)-4-phenylpiperazine be prepared according to C. B. POLLARD, J. Org. Chem. 24, 764, 1958.

(+)-N-[3-(α-Hydroxyiminobenzyl)phenyl]-3-(3-pyridyl)-1H,3H-pyrrolo[1,2-c]thiazole-7-carboxamide is obtained as described in Example 1.

EXAMPLE 3

A 50% strength dispersion (0.44 g) of sodium hydride in liquid paraffin is added at room temperature under a stream of nitrogen and with stirring to a solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (2 g) in anhydrous N,N-dimethylformamide (10 cc). A solution of 3-dimethylamino-1-chloropropane hydrochloride (0.72 g) in anhydrous N,N-dimethylformamide (20 cc) is then added in the course of approximately 1 minute. The solution is then stirred for 6 hours at room temperature, and thereafter treated with distilled water (10 cc). The solvent is evaporated off under reduced pressure (0.1 mm Hg; 13.5 Pa) at a temperature in the region of 50° C. The residue is taken up in acetone (100 cc). After 15 minutes, stirring at room temperature, the solid is separated by filtration and washed twice with acetone (40 cc in total). The filtrate is evaporated under reduced pressure (20 mm Hg; 2.7 kPa) at a temperature in the region of 50° C.). An orange residue (2.5 g) is obtained. This product is chromatographed on a column 3 cm in diameter containing silica (0.02–0.045 mm) (65 g). The column is eluted with a mixture of ethyl acetate and methanol (50:50 by volume) at a pressure of 0.5 bar (51 kPa), collecting 25-cc fractions. The first 19 fractions are discarded. The next 31 fractions are combined and concentrated to dryness under reduced pressure (20 mm Hg; 2.7 kPa) at a temperature in the region of 40° C. A product (1.3 g) is thereby obtained. This product is dissolved in ethyl ether (40 cc). The solution obtained is treated with a 4 N solution (1.65 cc) of hydrogen chloride gas in ethyl ether and stirred at a temperature in the region of 20° C. for 15 minutes. The crystals obtained are separated by filtration, washed 4 times with ethyl ether (50 cc in total) and dried under reduced pressure (0.1 mm Hg; 13.5 Pa) at a temperature in the region of 60° C. (+)-N-{3-[α-(3-Dimethylaminopropoxyimino)benzyl]phenyl}-3-(3-pyridyl)-1H,3H-pyrrolo[1,2-c]thiazole-7-carboxamide dihydrochloride (mixture of E and Z forms) (1.35 g) is thereby obtained in the form of cream-coloured crystals, m.p. 140° C.

(+)-N-[3-(α-Hydroxyiminobenzyl)phenyl]-3-(3-pyridyl)-1H,3H-pyrrolo[1,2-c]thiazole-7-carboxamide is obtained as described in Example 1.

EXAMPLE 4

A 50% strength dispersion (0.86 g) of sodium hydride in liquid paraffin is added at room temperature under a stream of nitrogen and with stirring to a solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (2.64 g) in anhydrous N,N-dimethylformamide (10 cc), followed by the addition of 1-(3-chloropropyl)piperidine hydrochloride (1 24 g) in small portions in the course of approximately 5 minutes. The solution is then stirred for 48 hours at a temperature in the region of 20° C. The solvent is evaporated off under reduced pressure (20 mm Hg; 2.7 kPa). A pasty orange residue (4.85 g) is thereby obtained, which is chromatographed on a column 4 cm in diameter containing silica (0.02–0.045 mm) (150 g). The column is eluted with a mixture of ethyl acetate and methanol (70:30 by volume) at a pressure of 0.5 bar (51 kPa), collecting 80-cc fractions. The first 10 fractions are discarded. The next 31 fractions are combined and concentrated to dryness under reduced pressure (20 mm Hg; 2.7 kPa) at a temperature in the region of 40° C. A product (2.8 g) is thereby obtained. This product is dissolved in ethyl acetate (30 cc). The insoluble matter is separated by filtration and the filtrate is evaporated under reduced pressure (20 mm Hg; 2.7 kPa) at a temperature in the region of 40° C. The product (2.70 g) obtained is dissolved in 1 N aqueous hydrochloric acid solution (15 cc). The solution obtained is filtered and then lyophilized. The 3.2 g thereby obtained are dissolved in distilled water (50 cc). The solution obtained is brought to a pH in the region of 8 by adding sodium bicarbonate and is then extracted 3 times with ethyl acetate (50 cc in total). The organic extracts are combined, dried over anhydrous magnesium sulphate, filtered and concentrated under reduced pressure (20 mm Hg; 2.7 kPa) at a temperature in the region of 35° C. A beige meringue-like product (2 g) is thereby obtained. This product is chromatographed on a column 3 cm in diameter containing silica (0.02–0.045 mm) (65 g). The column is eluted with ethyl acetate at a pressure of 0.5 bar (51 kPa), collecting 250-cc fractions. The first fraction is discarded. The next 12 fractions are combined and concentrated to dryness under reduced pressure (20 mm Hg; 2.7 kPa) at a temperature in the region of 40° C. A product (1.3 g) is thereby obtained, which is redissolved in acetonitrile (3 cc). The solution obtained is treated with ethyl ether (20 cc) and then with a 4 N solution (2 cc) of hydrogen chloride gas in ethyl ether, and stirred at a temperature in the region of 20° C. for 15 minutes. The crystals obtained are separated by filtration, washed 4 times with ethyl ether (50 cc in total) and dried under reduced pressure (0.1 mm Hg; 13.5 Pa) at a temperature in the region of 50° C. (+)-N-{3-[α-(3-Piperidinopropoxyimino)-benzyl]phenyl}-3-(3-pyridyl)-1H,3H-pyrrolo[1,2-c]thiazole-7-carboxamide dihydrochloride (mixture of E and Z forms) (1.3 g) is thereby obtained in the form of cream-coloured crystals, m.p. 142° C.

(+)-N-[3-(α-Hydroxyiminobenzyl)phenyl]-3-(3-pyridyl)-1H,3H-pyrrolo[1,2-c]thiazole-7-carboxamide is obtained as described in Example 1.

EXAMPLE 5

2-Morpholinoethoxyamine dihydrochloride (3.1 g) and sodium carbonate (1.5 g) are added with stirring to a solution, heated to reflux, of (+)-N-(3-(benzoyl)-phenyl]-3-(3-pyridyl)-1H,3H-pyrrolo[1,2-c]thiazole-7-carboxamide (5.9 g) in 1-propanol (100 cc). The suspension is stirred for 5 hours 30 minutes under reflux and then brought back to a temperature in the region of 20° C. The insoluble matter is separated by filtration and washed with 1-propanol (20 cc). The filtrate is concentrated under reduced pressure (20 mm Hg; 2.7 kPa) at a temperature in the region of 40° C. A pasty orange product (9 g) is thereby obtained. This product is chromatographed on a column 6 cm in diameter containing activated acidic alumina (0.050– 0.200 mm) (1 kg). The column is eluted with a mixture of ethyl acetate and cyclohexanone (50:50 by volume) at a pressure of 0.5 bar (51 kPa), collecting 500-cc fractions. The first 20 fractions are discarded; the next 10 fractions are combined and concentrated to dryness under reduced pressure (20 mm Hg; 2.7 kPa) at a temperature in the region of 40° C. A product (8.1 g) is thereby obtained. This product is chromatographed on a column 3 cm in diameter containing silica (0.02–0.045.mm) (125 g). The column is eluted with a mixture of ethyl acetate and methanol (90:10 by volume) at a pressure of 0.5 bar (51 kPa), collecting 25-cc fractions. The first 19 fractions are discarded and the next 7 fractions are combined and concentrated to dryness under reduced pressure (20 mm Hg; 2.7 kPa) at a temperature in the region of 40° C. A yellow meringue-like product (4 g) is thereby obtained. The product is chromatographed on a column 6 cm in diameter containing neutral alumina (0.100–0.125 mm) (65 g). The column is eluted with a mixture of ethyl acetate and cyclohexane (20:80 by volume), collecting 300-cc fractions. The first 3 fractions are discarded; the next 3 are combined and concentrated to dryness under reduced pressure (20 mm Hg; 2.7 kPa). A product (2 g) is obtained in the form of a white meringue-like material. This product is chromatographed on a column 4 cm in diameter containing neutral alumina (0.100–0.125 mm) (25 g). The column is eluted with a mixture of ethyl acetate and cyclohexane (50:50 by volume), collecting 100-cc fractions. The first 9 fractions are discarded; the next 7 are concentrated to dryness under reduced pressure (20 mm Hg; 2.7 kPa) at a temperature in the region of 40° C. A product (1.55 g) is obtained. 850 mg of this product are dissolved in a 0.21 N aqueous solution (15 cc) of methanesulphonic acid. The aqueous solution obtained is lyophilized. (+)-N-{3-[α-(2-Morpholinoethoxyimino)benzyl]phenyl}-3-(3-pyridyl)-1H,3H-pyrrolo[1,2-c]thiazole-7-carboxamide dimethanesulphonate (mixture of E and Z forms) (0.98 g) is thereby obtained in the form of pale yellow crystals, m.p. 122° C.

2-Morpholinoethoxyamine dihydrochloride may be prepared according to D. FAVARA et al., Il Farmaco, Ed. Sci., 42, 697, 1987.

(+)-N-(3-Benzoylphenyl)-3-(3-pyridyl)-1H,3H-pyrrolo[1,2-c]thiazole-7-carboxamide is obtained as described in the European Patent Application published under No. 0,253,711.

EXAMPLE 6

3-(4-Methyl-1-piperazinyl)propoxyamine trihydrochloride (6.2 g) and sodium carbonate (3.8 g) are added with stirring to a solution, heated to a temperature in the region of 75° C., of (+)-N-(3-benzoylphenyl)-3-(3-pyridyl)-1H,3H-pyrrolo[1,2-c]thiazole-7-carboxamide (9.3 g) in 1-propanol (160 cc). The suspension obtained is heated to reflux for 29 hours and the reaction mixture is then concentrated to dryness under reduced pressure (20 mm Hg; 2.7 kPa) at a temperature in the region of 60° C. The residue obtained is taken up with a mixture of water (300 cc) and methylene chloride (300 cc). The organic phase is separated and the aqueous phase is extracted twice with methylene chloride (600 cc in total). The organic extracts are combined, washed twice with distilled water (600 cc in total), dried over anhydrous magnesium sulphate, filtered and concentrated to dryness under reduced pressure (20 mm Hg; 2.7 kPa) at a temperature in the region of 50° C. A crude product (14.3 g) is thereby obtained. This product is chromatographed on a column 6 cm in diameter containing silica (0.02–0.045 mm) (450 g). The column is eluted with a mixture of methylene chloride and methanol (50:50 by volume) at a pressure of 0.5 bar (51 kPa), collecting 500-cc fractions. The first 7 fractions are discarded. The next 13 fractions are combined and concentrated to dryness under reduced pressure (20 mm Hg; 2.7 kPa) at a temperature in the region of 40° C. A product (7.2 g) is thereby obtained. This product is combined with another sample (0.8 g) originating from an earlier preparation, and is dissolved in acetone (200 cc). The solution obtained is added, at a temperature in the region of 20° C., to a solution of oxalic acid (2.5 g) in acetone (100 cc). The suspension obtained is stirred at a temperature in the region of 20° C. for 1 hour 30 minutes; the crystals which appear are separated by filtration, washed 3 times with acetone (150 cc in total) and then twice with ethyl ether (100 cc in total and finally dried under reduced pressure (20 mm Hg; 2.7 kPa) at a temperature in the region of 20° C. (+)-N-3-(α-[3-(4-Methyl-1-piperazinyl)propoxyimino]-benzyl}phenyl-3-(3--pyridyl)-1H,3H-pyrrolo[1,2-c]thiazole-7-carboxamide acid dioxalate (mixture of E and Z forms) (9.1 g) is thereby obtained in the form of white crystals, m.p. 190° C.

(+)-N-[3-{-α-[3-(4-Methyl-1-piperazinyl)propoxyimino]benzyl}phenyl]-3-(3-pyridyl)-1H,3H-pyrrolo[1,2-c]thiazole-7-carboxamide (1.16 g), in base form, is dissolved in ethyl acetate (10 cc). The solution obtained is treated with decolorizing charcoal (50 mg) and filtered. The insoluble matter is washed with ethyl acetate (10 cc). The filtrate is treated with 4 N ethereal hydrogen chloride (1 cc) and stirred at a temperature in the region of 20° C. for 15 minutes. The crystals which have appeared ar separated by filtration, washed 3 times with ethyl acetate (9 cc in total) and dried under reduced pressure (0.1 mm Hg; 13.5 Pa) at a temperature in the region of 20° C. (+)-N-[3-{α-[3-(4-Methyl-1-piperazinyl)propoxyimino]benzyl}phenyl]-3--(3-pyridyl)-1H,3H-pyrrolo[1,2-c]thiazole-7-carboxamide dihydrochloride (1.27 g), in the state of a mixture of E and Z forms, is thereby obtained in the form of cream-coloured crystals, m.p. 150°-155° C.

(+)-N-(3-Benzoylphenyl)-3- (3-pyridyl)-1H,3H-pyrrolo[1,2-c]thiazole-7-carboxamide is obtained as described in the European Patent Application published under No. 0,253,711.

3-(4-Methyl-1-piperazinyl)propoxyamine trihydrochloride may be obtained in the following manner: a solution of N-[3-(4-methyl-1-piperazinyl)propoxy]phthalimide (5.7 g) in 6 N hydrochloric acid (30 cc) is heated to reflux for 3 hours. After 18 hours' stirring at a temperature in the region of 20° C., the suspension obtained is filtered and the filtrate is concentrated to dryness under reduced pressure (20 mm Hg; 2.7 kPa) at a temperature in the region of 60° C. A crude product (6 g) is thereby obtained, which is resuspended in ethanol (30 cc). The crystals which appear are separated by filtration, washed 3 times with ethanol (45 cc in total) and then 3 times with ethyl ether (75 cc in total) and finally dried under reduced pressure (20 mm Hg; 2.7 kPa) at a temperature in the region of 20° C. 3-(4-Methyl-1-piperazinyl)propoxyamine trihydrochloride (3.4 g) is thereby obtained in the form of cream-coloured crystals, m.p. 240° C.

N-[3-(4-Methyl-1-piperazinyl)propoxy]phthalimide may be obtained in the following manner: a solution of 1-(3-hydroxypropyl)-4-methylpiperazine (8.4 g), N-hydroxyphthalimide (8.2 g) and triphenylphosphine (13.1 g) in tetrahydrofuran (120 cc) is cooled to a temperature in the region of 0° C. and ethyl azodicarboxylate (10.1 g) is added in the course of 30 minutes. The solution obtained is stirred at a temperature in the region of 20° C. for 18 hours and is then concentrated to dryness under reduced pressure (20 mm Hg; 2.7 kPa) at a temperature in the region of 60° C. The crude oil obtained is chromatographed on a column 5 cm in diameter containing silica (0.063–0.2 mm) (400 g). The column is eluted with mixtures of ethyl acetate and methanol, collecting 500-cc fractions. The first 5 fractions originating from elution with pure ethyl acetate and the next 5 fractions originating from elution with a mixture of ethyl acetate and methanol (70:30 by volume) are discarded. The next fraction originating from elution with a mixture of ethyl acetate and methanol (70:30 by volume), the next 5 fractions originating from elution with a mixture of ethyl acetate and methanol (50:50 by volume) and the next 2 fractions originating from elution with pure methanol are combined and concentrated to dryness under reduced pressure (20 mm Hg; 2.7 kPa) at a temperature in the region of 60° C. N-[3-(4-Methyl-1-piperazinyl)propoxy]phthalimide (11.4 g) is thereby obtained in the form of a red oil (Rf=0.2; thin-layer chromatography on silica, eluent: ethyl acetate/-methanol, 50:50 by volume).

Separation of the E and Z forms may be performed in the following manner: (+)-N-3-{-α-[3-(4-methyl-1-piperazinyl)propoxyimino-]benzyl}phenyl--3-(3-pyridyl)1H,3H-pyrrolo[1,2-c]thiazole-7-carboxamide (mixture of E and Z forms), in the state of acid dioxalate, (50 mg), obtained above, is dissolved in a mixture (2 cc) of acetonitrile and water (50:50 by volume). The solution obtained is injected onto a chromatography column 25 cm long and 2 cm in diameter packed with a stationary phase of $C_{18}$ grafted silica [ULTRBASE (registered trade name of the Société Francaise de Chromatographie sur colonne, Neuilly-Plaisance, France) silica]. The column is eluted with a mixture of acetonitrile, water and triethylamine (40:60:0.5 by volume) at a flow rate of 5 cc per minute. The eluates are analysed by ultraviolet absorbance measurement at 270 nm. The two isomers are detected at respective retention times of 90 and 110 minutes. The eluates containing the desired products are combined and concentrated to dryness under reduced pressure (20 mm Hg; 2.7 kPa) at a temperature in the region of 40° C. and dried under reduced pressure (1 mm Hg; 0.7 kPa) at 20° C. overnight. Form A (14 mg) and form B (18 mg) of (+)-N-3-(α-[3-(4-methyl-1-piperazinyl)propoxyimino]benzyl}phenyl-3-(3-pyridyl)-1H,3H-pyrrolo[1,2-c]thiazole-7-carboxamide are thereby obtained in the state of acid dioxalates.

(+)-N-[3-{α-[3-(4-Methyl-1-piperazinyl)propoxyimino] benzyl}phenyl-3-(3-pyridyl)-1H,3H-pyrrolo[1,2-c]thiazole-7-carboxamide acid dioxalate form A (150 mg), obtained by repetition of the above operation, is dissolved in 1 N sodium hydroxide (5 cc). The solution is extracted 3 times with ethyl acetate (25 cc in total). The organic extracts are combined, dried over anhydrous magnesium sulphate, filtered and concentrated to dryness under reduced pressure (20 mm Hg; 2.7 kPa) at a temperature in the region of 45° C. The product obtained (145 mg) is dissolved in 0.1 N hydrochloric acid (5.23 cc) and the solution obtained is lyophilized. (+)-N-3-{-α-[3-(4-Methyl-1-piperazinyl)propoxyimino]benzyl}phenyl-3-(3-pyridyl)-1H,3H-pyrrolo[1,2-c]thiazole-7-carboxamide form A (153 mg) is thereby obtained in the state of a dihydrochloride.

(+)-N-[3-{α-[3-(4-Methyl-1-piperazinyl)propoxyimino]benzyl}phenyl-3-(3-pyridyl)-1H,3H-pyrrolo[1,2-c]thiazole-7-carboxamide acid dioxalate form B (120 mg), obtained by repetition of the above operation, is dissolved in 1 N sodium hydroxide (5 cc). The solution is extracted 3 times with ethyl acetate (30 cc in total). The organic extracts are combined, dried over anhydrous magnesium sulphate, filtered and concentrated under reduced pressure (20 mm Hg; 2.7 kPa) at a temperature in the region of 45° C. The product obtained (100 mg) is dissolved in 0.1 N hydrochloric acid (3.6 cc) and the solution obtained is lyophilized. (+)-N-3--{α-[3-(4-Methyl-1-piperazinyl)propoxyimino]benzyl}phenyl-3-(3-pyridyl)-1H,3H-pyrrolo[1,2-c]thiazole-7-carboxamide form B (108 mg) is thereby obtained in the state of a dihydrochloride.

The two forms were identified by their proton NMR spectrum (200 Mhz, DMSO, d in ppm, J in Hz) with the following indications: S=singlet, D doublet, T=triplet, Cx=complex, Mt=multiplet, DD=double doublet, DT=double triplet.

Form A 2.2 (Cx, 2H: -CH$_2$-CH$_2$-); 2.86 (S, 3H; .NCH$_3$); 3.24 (Cx, 2H: -CH$_2$-CH$_2$-N); 3.3 to 3.9 (Mt, 8H: piperazine.NCH$_2$-); 4.24 (T, J=7, 2H: -OCH$_2$-); 4.45 and 4.63 (D, J=15 and DD, J=15 and 1, 1H each: pyrrolothiazole CH$_2$); 6.74 (D, J=2.5, 1H: CH at 6-position of pyrrolothiazole); 6.86 (D, J=1, 1H: CH at 3-position of pyrrolothiazole); 7.09 (DT, J=8, 1H, aromatic para to -NH-CO-); 7.11 (D, J=2.5, 1H: CH at 5-position of pyrrolothiazole); 7.4 to 7.6 (Mt, 6H: aromatic); 7.8 (Mt, 2H: H at 5-position of pyridine and aromatic ortho to -NH-CO- and to .C=N-); 7.92 (broad D, J=8, 1H: H at 4-position of pyridine); 8.01 (DT, J=8, 1H: aromatic ortho to -NH-CO-); 8.71 (broad S, 1H: H at 2-position of pyridine); 8.78 (broad D, J=5, 1H: H at 6-position of pyridine); 9.84 (S, 1H: -CONH-); ~11.8 (extended Cx, ~1H: .NHs-).

Form B 2.19 (Mt, 2H: -CH$_2$-CH$_2$-CH$_2$); 2.87 (S, 3H: .NCH$_3$); 3.20 (Cx, 2H: -CH$_2$-CH$_2$-N); 3.3 to 3.9 (Mt, 8H: piperazine .NCH$_2$-); 4.23 (T, J=7, 2H: -OCH$_2$-); 4.44 and 4.63 (D, J=15 and DD, J=15 and 1, 1H each: pyrrolothiazole CH$_2$); 6.73 (D, J=2.5, 1H: CH at 6-position of pyrrolothiazole); 6.86 (D, J=1, 1H: CH at 3-position of pyrrolothiazole); 7.08 (D, J=2.5, 1H: CH at 5-position of pyrrolothiazole); 7.08 (Mt, 1H: aromatic para to -NH-CO-); 7.3 to 7.65 (Mt, 6H: aromatic); 7.77 (DD, J=8 and 5, 1H: H at 5-position of pyridine); 7.85 to 8.05 (Mt, 3H: aromatic ortho to -NH-CO- and at 4-position of pyridine); 8.7 (broad S, 1H: H at 2-position of pyridine); 8.77 (D, J=5, 1H: H at 6-position of pyridine); 9.79 (S, 1H: -CONH-); ~11.7 (extended Cx, ~1H: .NHs-).

EXAMPLE 7

2-Dimethylaminoethoxyamine dihydrochloride (3.8 g) and sodium carbonate (2.3 g) are added with stirring to a solution, heated to a temperature in the region of 80° C., of (+)-N-(3-benzoylphen-Yl)-3-(3-pyridyl)-1H,3H-pyrrolo[1,2-c]thiazole-7-carboxamide (9.15 g) in 1-propanol (110 cc). The suspension obtained is heated to reflux for 8 hours and then, after the addition of sodium carbonate (0.23 g), for a further 8 hours. The reaction mixture is concentrated to dryness under reduced pressure (20 mm Hg; 2.7 kPa) at a temperature in the region of 60° C. After cooling, the residue obtained is taken up with a mixture of water (250 cc) and methylene chloride (250 cc). The organic phase is separated and the aqueous phase is extracted twice with methylene chloride (500 cc in total). The organic extracts are combined, washed twice with distilled water (500 cc in total), dried over anhydrous magnesium sulphate, filtered and concentrated to dryness under reduced pressure (20 mm Hg; 2.7 kPa) at a temperature in the region of 50° C. A crude product (11 g) is thereby obtained. This product is chromatographed on a column 6 cm in diameter containing silica (0.02–0.045 mm) (450 g). The column is eluted with mixtures of methylene chloride and methanol at a pressure of 0.5 bar (51 kPa), collecting 500-cc fractions. The first 4 fractions originating from elution with a mixture of methylene chloride and methanol (90:10 by volume) are discarded. The next 9 fractions originating from elution with a mixture of methylene chloride and methanol (90:10 by volume) and the next 7 fractions originating from elution with a mixture of methylene chloride and methanol (80:20 by volume) are combined and concentrated to dryness under reduced pressure (20 mm Hg; 2.7 kPa) at a temperature in the region of 50° C. A product (5.9 g) is thereby obtained. 4 g of this product are chromatographed on a silica column 6 cm in diameter containing silica (0.02–0.045 mm) (450 g). The column is eluted with mixtures of ethyl acetate and methanol at a pressure of 0.5 bar (51 kPa), collecting 500-cc fractions. The first 10 fractions originating from elution with a mixture of ethyl acetate and methanol (50:50 by volume) are discarded; the next 16 fractions originating from elution with pure methanol are combined and concentrated to dryness under reduced pressure (20 mm Hg; 2.7 kPa) at a temperature in the region of 50° C. A product (2.9 g) is thereby obtained, which is taken up with 0.1 N aqueous hydrochloric acid solution (57 cc). The cloudy solution obtained is brought to a pH in the region of 8 by adding sodium bicarbonate and is then extracted 3 times with methylene chloride (750 cc in total). The organic extracts are combined, dried over anhydrous magnesium sulphate, filtered and concentrated under reduced pressure (20 mm Hg; 2.7 kPa) at a temperature in the region of 50° C. A product (2.2 g) is thereby obtained, which is redissolved in 0.1 N aqueous hydrochloric acid solution (43 cc). The solution is then lyophilized. (+)-N-{3-[α-(2-Dimethylaminoethoxyimino)-benzyl]phenyl}-3-(3-pyridyl)-1H,3H-pyrrolo[1,2-c]thiazole-7-carboxamide hydrochloride (mixture of E and Z forms) (2.1 g) is thereby obtained in the form of a pale yellow lyophilisate.

(+)-N-(3-Benzoylphenyl)-3-(3-pyridyl)-1H,3H-pyrrolo[1,2-c]thiazole-7-carboxamide is obtained as described in the European Patent Application published under No. 0,253,711.

2-Dimethylaminoethoxyamine dihydrochloride may be obtained according to the method described by D. FAVARA et al., Il Farmaco, Ed. Sci., 42, 697 (1987).

EXAMPLE 8

3-Morpholinopropoxyamine dihydrochloride (1.6 g) and sodium carbonate (0.74 g) are added with stirring to a solution, heated to a temperature in the region of 70° C., of (+)-N-(3-benzoylphenyl)-3-(3-pyridyl)-1H,3H-pyrrolo[1,2-c]thiazole-7-carboxamide (3 g) in 1-propanol (50 cc). The suspension obtained is heated to reflux for 8 hours, the reaction mixture is then filtered and the filtrate is concentrated to dryness under reduced pressure (20 mm Hg; 2.7 kPa) at a temperature in the region of 40° C. A crude product (4.7 g) is thereby obtained. This product is chromatographed on a column 5 cm in diameter containing silica (0.02–0.045 mm) (500 g). The column is eluted with a mixture of ethyl acetate and methanol (50:50 by volume) at a pressure of 0.5 bar (51 kPa), collecting 500-cc fractions. The first 26 fractions are discarded; the next 14 fractions are combined and concentrated to dryness under reduced pressure (20 mm Hg; 2.7 kPa) at a temperature in the region of 40° C. The crude product obtained is taken up with ethanol (20 cc). The suspension obtained is filtered and the filtrate obtained is concentrated to dryness under reduced pressure (20 mm Hg; 2.7 kPa) at a temperature in the region of 60° C. A product (1.08 g) is thereby obtained, which is taken up with a 0.205 N aqueous solution (9.3 cc) of methanesulphonic acid. The cloudy solution is filtered and the filtrate is lyophilized. (+)-N-{3-[α-(3-Morpholinopropoxyimino)benzyl]phenyl}-3-(3-pyridyl)-1H,3H-pyrrolo[1,2-c]thiazole-7-carboxamide methanesulphonate (mixture of E and Z forms) (1.2 g) is thereby obtained in the form of a beige lyophilisate.

(+)-N-(3-Benzoylphenyl)-3-(3-pyridyl)-1H,3H-pyrrolo[1,2-c]thiazole-7-carboxamide is obtained as described in the European Patent Application published under No. 0,253,711.

3-Morpholinopropoxyamine dihydrochloride may be prepared in the following manner: a solution of N-(3-morpholinopropoxy)phthalimide (13.8 g) in 6 N hydrochloric acid (50 cc) is heated to reflux for 6 hours. After 18 hours' stirring at a temperature in the region of 20° C., the suspension obtained is filtered and the filtrate obtained is concentrated to dryness under reduced pressure (20 mm Hg; 2.7 kPa) at a temperature in the region of 50° C. A crude product (6.8 g) is thereby obtained, which is suspended in ethanol (10 cc). The crystals which appear are separated by filtration and then dried under reduced pressure (20 mm Hg; 2.7 kPa) at a temperature in the region of 20° C. 3-Morpholinopropoxyamine dihydrochloride (6.1 g) is thereby obtained in the form of cream-coloured crystals, m.p. 160° C.

N-(3-Morpholinopropoxy)phthalimide may be obtained in the following manner: solution of 3-morpholinopropanol (27.5 g), N-hydroxyphthalimide (30.2 g) and triphenylphosphine (47.2 g) in tetrahydrofuran (400 cc) is cooled to a temperature in the region of 0° C. and ethyl azodicarboxylate (37.65 g) is added in the course of 1 hour 30 minutes. The solution obtained is stirred at a temperature in the region of 20° C. for 18 hours and is then concentrated to dryness under reduced pressure (20 mm Hg; 2.7 kPa) at a temperature in the region of 40° C. The residue is taken up with ethyl acetate (500 cc) and the suspension obtained is filtered. The filtrate is extracted with N aqueous hydrochloric acid solution (200 cc). The aqueous phase is separated after settling has taken place and then extracted 3 times with ethyl acetate (600 cc in total). The aqueous phase is brought to a pH in the region of 10 by adding N aqueous sodium hydroxide solution and is extracted 3 times with ethyl acetate (300 cc in total). The organic extracts are combined, washed 3 times with distilled water (150 cc in total), dried over anhydrous magnesium sulphate, filtered and concentrated to dryness under reduced pressure (20 mm Hg; 2.7 kPa) at a temperature in the region of 40° C. A crude product (25.8 g) is thereby obtained, which is chromatographed on a column 8 cm in diameter containing silica (0.060 mm) (1 kg). The column is eluted with pure ethyl acetate, collecting 500-cc fractions. The first 12 fractions are discarded; the next 48 fractions are combined and concentrated to dryness under reduced pressure (20 mm Hg; 2.7 kPa) at a temperature in the region of 40° C. N-(3-Morpholinopropoxy)phthalimide (15.5 g) is thereby obtained in the form of white crystals, m.p. 98° C. 3-Morpholinopropanol may be obtained according to O. HROMATKA, Ber., 75, 131, (1942).

EXAMPLE 9

2-(4-Methyl-1-piperazinyl)ethoxyamine trihydrochloride (3 g) and sodium carbonate (1.8 g) are added with stirring to a solution, heated to a temperature in the region of 70° C., of (+)-N-(3-benzoylphenyl)-3-(3-pyridyl)-1H,3H-pyrrolo[1,2-c]thiazole-7-carboxamide (4.7 g) in 1-propanol (85 cc). The suspension obtained is heated to reflux for 10 hours and the reaction mixture is then concentrated under reduced pressure (20 mm Hg; 2.7 kPa) at a temperature in the region of 40° C. The residue obtained is taken up with N aqueous hydrochloric acid solution (100 cc). The solution obtained is extracted 3 times with ethyl ether (150 cc in total), brought to a pH in the region of 7 by adding saturated aqueous sodium bicarbonate solution and extracted 3 times with ethyl ether (300 cc in total). The ether extracts are combined, washed with distilled water (100 cc), dried over anhydrous magnesium sulphate, filtered and concentrated to dryness under reduced pressure (20 mm Hg; 2.7 kPa) at a temperature in the region of 40° C. A crude product (3.1 g) is thereby obtained, which is chromatographed on a column 5 cm in diameter containing silica (0.02–0.045 mm) (300 g). The column is eluted with a mixture of acetonitrile and ammonia solution (d=0.92) (95:5 by volume) at a pressure of 0.5 bar (51 kPa), collecting 200-cc fractions. The first 10 fractions are discarded. The next 2 fractions are combined and concentrated to dryness under reduced pressure (20 mm Hg; 2.7 kPa) at a temperature in the region of 40° C. A product (1.55 g) is thereby obtained. This product is redissolved in acetone (5 cc). The solution obtained is added, at a temperature in the region of 20° C., to a solution of oxalic acid (0.46 g) in acetone (10 cc). The suspension obtained is stirred at a temperature in the region of 20° C. for 30 minutes and the crystals which appear are then separated by filtration, washed twice with acetone (5 cc in total) and dried under reduced pressure (20 mm Hg; 2.7 kPa) at a temperature in the region of 20° C. (+)-N-3-{α-[2-(4-Methyl-1-piperazinyl)ethoxyimino]benzyl}phenyl-3-(3-pyridyl)-1H,3H-pyrrolo[1,2-c]thiazole-7-carboxamide acid dioxalate (mixture of E and Z forms) (1.7 g) is thereby obtained in the form of white crystals, m.p. 172° C.

(+)-N-(3-Benzoylphenyl)-3-(3-pyridyl)-1H,3H-pyrrolo[1,2-c]thiazole-7-carboxamide is obtained as described in the European Patent Application published under No. 0,253,711.

2-(4-Methyl-1-piperazinyl)ethoxyamine trihydrochloride may be obtained according to the method described by R₄ CRICCHIO et al., J. Med. Chem. 17, 396 (1974).

EXAMPLE 10

(1-Methyl-4-piperidyloxy)amine dihydrochloride (2.1 g) and sodium carbonate (0.72 g) are added to a solution, heated to a temperature in the region of 70° C., of (+)-N-(3-benzoylphenyl)-3-(3-pyridyl)-1H,3H-pyrrolo[1,2-c]thiazole-7-carboxamide (3 g) in 1-propanol (50 cc). The suspension obtained is heated to a temperature in the region of 90° C. for 2 hours 30 minutes and is then stirred at a temperature in the region of 20° C. for 18 hours, and finally filtered. The filtrate is concentrated under reduced pressure (20 mm Hg; 2.7 kPa) at a temperature in the region of 35° C. A crude product (6.1 g) is thereby obtained, which is taken up with acetonitrile (60 cc). The crystals obtained are separated by filtration and taken up with a mixture of N sodium hydroxide (50 cc) and ethyl acetate (20 cc). The organic phase is separated after settling has taken place and the aqueous phase is extracted twice with ethyl acetate (40 cc in total). The organic extracts are combined, washed 3 times with distilled water (45 cc in total), dried over anhydrous magnesium sulphate, filtered and concentrated to dryness under reduced pressure (20 mm Hg; 2.7 kPa) at a temperature in the region of 35° C. The product obtained (3.2 g) is chromatographed on a column 4 cm in diameter containing silica (0.02–0.045 mm) (35 g). The column is eluted with a mixture (200 cc) of ethyl acetate and methanol (60:30 by volume). The fraction obtained is concentrated to dryness under reduced pressure (20 mm Hg; 2.7 kPa) at a temperature in the region of 35° C. A product (1.25 g) is thereby obtained, which is redissolved in ethyl acetate (5 cc). A 5.6 N solution (0.42 cc) of hydrogen chloride gas in ethyl ether is then added to the solution The crystals which appear are separated by filtration and dried under reduced pressure (20 mm Hg; 2.7 kPa) at a temperature in the region of 20° C. A product (0.82 g) is thereby obtained, which is redissolved in distilled water (20 cc). The solution obtained is brought to a pH in the region of 10 by adding 2 N aqueous sodium hydroxide solution and is then extracted 3 times with ethyl acetate (30 cc in total). The organic extracts are combined, washed twice with distilled water (20 cc in total), dried over anhydrous magnesium sulphate, filtered and concentrated to dryness under reduced pressure (20 mm Hg; 2.7 kPa) at a temperature in the region of 40° C. The 0.65 g obtained is combined with a product (0.55 g) obtained previously according to the same method and chromatographed on a column 4 cm in diameter containing silica (0.02–0.045 mm) (300 g). The column is eluted with a mixture of ethyl acetate and diethylamine (95:5 by volume) at a pressure of 0.5 bar (51 kPa), collecting 500-cc fractions. The first 7 fractions are discarded. The next 5 fractions are combined and concentrated to dryness under reduced pressure (20 mm Hg; 2.7 kPa) at a temperature in the region of 40° C. A product (880 mg) is thereby obtained, which is dissolved in 0.1 N aqueous hydrochloric acid solution (16.4 cc). The solution obtained is extracted twice with ethyl ether (40 cc in total) and the aqueous phase is brought to a pH in the region of 10 by adding N aqueous sodium hydroxide solution and is then extracted 3 times with ethyl acetate (60 cc in total). The organic extracts are combined, washed twice with distilled water (20 cc in total), dried over anhydrous magnesium sulphate, filtered and concentrated to dryness under reduced pressure (20 mm Hg; 2.7 kPa) at a temperature in the region of 40° C. A product (630 mg) is thereby obtained 530 mg of this product are dissolved in acetone (5 cc). The solution obtained is added to a solution of oxalic acid (0.17 g) in acetone (5 cc). The crystals which appear are separated by filtration, washed with acetone (2 cc) and then with a mixture (2 cc) of acetone and ethyl ether (50:50 by volume) and finally dried under reduced pressure (20 mm Hg; 2.7 kPa) at a temperature in the region of 20° C. (+)-N-[3-{α-[(1-Methyl-4-piperidyloxy)imino]benzyl}phenyl]-3-(3-pyridyl)-1H,3H-pyrrolo[1,2-c]-thiazole- 7-carboxamide acid dioxalate (mixture of E and Z forms) (570 mg) is thereby obtained in the form of cream-coloured crystals, m.p. 170° C.

(+)-N-[3{α-[(1-Methyl-4-piperidyloxy)imino]benzyl]phenyl]-3-(3-pyridyl)-1H,3H-pyrrolo[1,2-c]thiazole-7-carboxamide (1.0 g), in base form, is dissolved in absolute ethanol (4 cc). The solution obtained is treated with 4 N ethereal hydrogen chloride (0.93 cc) and diluted with ethyl acetate (20 cc) and then diethyl ether (100 cc). After 15 hours' stirring at a temperature in the region of 20° C., the crystals which appear are separated by filtration, washed 4 times with diethyl ether (20 cc in total) and dried in the air at a temperature in the region of 20° C. (+)-N-[3-(α-[(1-Methyl-4-piperidyloxy)imino]benzyl}phenyl-3-(3-pyridyl)-1H,3H-pyrrolo[1,2-c]thiazole-7-carboxamide dihydrochloride (1.1 g), in the state of a mixture of E and Z forms, is thereby obtained in the form of cream-coloured crystals, m.p. 200°–205° C.

(+)-N-(3-Benzoylphenyl)-3-(3-pyridyl)-1H,3H-pyrrolo[1,2-c]thiazole-7-carboxamide is obtained according to the method described in the European Patent Application published under No. 0,253,711.

(1-Methyl-4-piperidyloxy)amine dihydrochloride may be obtained in the following manner: an aqueous solution of N-(1-methyl-4-piperidyloxy)phthalimide (18.7 g) in 6 N aqueous hydrochloric acid solution (100 cc) is heated to reflux for 3 hours. The suspension obtained is filtered and the filtrate is concentrated to dryness under reduced pressure (20 mm Hg; 2.7 kPa) at a temperature in the region of 45° C. The product obtained is suspended in ethanol (100 cc) and the crystals which appear are separated by filtration, washed twice with ethanol (100 cc in total) and dried under reduced pressure (20 mm Hg; 2.7 kPa) at a temperature in the region of 20° C. (1-Methyl-4-piperidyloxy)amine dihydrochloride (11.2 g) is thereby obtained in the form of white crystals, m.p. 220° C.

N-(1-Methyl-4-piperidyloxy)phthalimide may be obtained in the following manner: diethyl azodicarboxylate (53.8 g) is added in the course of 90 minutes at a temperature in the region of 0° C. to a suspension of 4-hydroxy-1-methylpiperidine (30.6 g), N-hydroxyphthalimide (43.7 g) and triphenylphosphine (68.3 g) in tetrahydrofuran (450 cc). The suspension obtained is stirred at a temperature in the region of 20° C. for 18 hours and the reaction mixture is then concentrated to dryness under reduced pressure (20 mm Hg; 2.7 kPa) at a temperature in the region of 40° C. The product obtained is taken up with ethyl acetate (500 cc) and the suspension obtained is filtered. The filtrate is concentrated to dryness under reduced pressure (20 mm Hg; 2.7 kPa) at a temperature in the region of 40° C. The product obtained is redissolved in N aqueous hydrochloric acid solution (500 cc). The suspension obtained is filtered and the filtrate is extracted 3 times with ethyl ether (300 cc in total) and brought to a pH in the range of 10 by adding N aqueous sodium hydroxide solution (500 cc) The crystals which appear are separated by filtration, washed 3 times with distilled water (300 cc in total) and dried under reduced pressure (20 mm Hg; 2.7 kPa) at a temperature in the region of 20° C. N-(1-Methyl-4-piperidyloxy)phthalimide (19 g) is thereby obtained in the form of beige crystals, m.p. 90° C.

EXAMPLE 11

A 50% strength dispersion (0.36 g) of sodium hydride in liquid paraffin is added at room temperature under a stream of nitrogen and with stirring to a solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (3 g) in anhydrous N,N-dimethylformamide (15 cc). A solution of 3-(benzylethylamino)propyl para-toluenesulphonate (2.61 g) in anhydrous N,N-dimethylformamide (13 cc) is then added in the course of approximately 5 minutes and the solution is thereafter stirred for 12 hours at a temperature in the region of 20° C. Distilled water (250 cc) is then added and the solution is extracted 3 times with ethyl acetate (240 cc in total). The organic extracts are combined and washed with 0.1 N aqueous hydrochloric acid solution (80 cc). The aqueous phase is then brought to pH 8 by adding 1 N aqueous sodium hydroxide solution and the solution is extracted 3 times with ethyl acetate (240 cc in total). The organic extracts are combined, dried over anhydrous magnesium sulphate, filtered and concentrated to dryness under reduced pressure (20 mm Hg; 2.7 kPa) at a temperature in the region of 45° C. A pasty brown residue (1.61 g) is thereby obtained. This product is chromatographed on a column 4 cm in diameter containing neutral alumina (0.032–0.063 mm) (200 g). The column is eluted with ethyl acetate (2.8 litres) and then with a mixture (750 cc) of ethyl acetate and methanol (95:5 by volume) at a pressure of 0.5 bar (51 kPa), collecting 50-cc fractions. The first 27 fractions are discarded. The next 39 fractions are combined and concentrated to dryness under reduced pressure (20 mm Hg; 2.7 kPa) at a temperature in the region of 40° C. A product (1 g) is thereby obtained, which is dissolved in ethyl acetate (5 cc). The solution is treated with decolorizing charcoal (0.1 g) and then filtered while hot, and the filter is rinsed with ethyl acetate (5 cc). A 4 N solution (0.8 cc) of hydrogen chloride gas in ethyl ether is added to this solution and the mixture is stirred at a temperature in the region of 20° C. for 15 minutes. The crystals obtained are separated by filtration, washed 4 times with ethyl ether (50 cc in total) and dried under reduced pressure (0.1 mm Hg; 13.5 Pa) at a temperature in the region of 60° C. (+)-N-[ 3-{α-[3-(Benzylethylamino)propoxyimino]benzyl}phenyl-3-(3-pyridyl)-1H,3H-pyrrolo[1,2-c]thiazole-7-carboxamide dihydrochloride (0.96 g), in the state of a mixture of E and Z forms, is thereby obtained in the form of cream-coloured crystals, m.p. 175° C.

(+)-N-(3-Benzoylphenyl)-3-(3-pyridyl)-1H,3H-pyrrolo[1,2-c]thiazole-7-carboxamide is obtained as described in the European Patent Application published under No. 0,253,711.

3-(Benzylethylamino)propyl tosylate may be prepared in the following manner: a solution of paratoluenesulphonyl chloride (3.8 g) in pyridine (10 cc) is added with stirring in the course of approximately 20 minutes to a solution of 3-(benzylethylamino)propanol (3.86 g) in pyridine (10 cc), and the reaction mixture is stirred for 20 minutes at a temperature in the region of 20° C. The solution is treated with distilled water (200 cc) and is then extracted twice with ethyl acetate (160 cc in total). The organic extracts are combined, washed with distilled water (200 cc in total), then dried over anhydrous magnesium sulphate, filtered and concentrated to dryness under reduced pressure (20 mm Hg; 2.7 kPa) at a temperature in the region of 40° C. 3-(Benzylethylamino)propyl paratoluenesulphonate (4.78 g) is obtained in the form of an orange-coloured oil, which is employed in the crude state in the subsequent syntheses.

3-(Benzylethylamino)propanol may be prepared in the following manner: a solution of benzylethylamine (6.76 g), 3-chloropropyl acetate (6.15 cc) and sodium carbonate (5.3 g) in 2-propanol (25 cc) is heated to reflux with stirring for 48 hours and then cooled to a temperature in the region of 20° C. The sodium chloride formed is separated by filtration and the solvent is evaporated to dryness under reduced pressure (20 mm Hg; 2.7 kPa) at a temperature in the region of 45° C. An orange-coloured oil (17.4 g) is obtained, which is taken up with distilled water (30 cc) and 10 N aqueous hydrochloric acid solution (30 cc). The solution obtained is heated to reflux for 6 hours and then cooled to a temperature in the region of 20° C. Decolorizing charcoal (200 mg) is added. The solution is filtered and the filter is rinsed with distilled water (50 cc in total). Ammonia solution (d=0.92) (40 cc) is added and the mixture is extracted 3 times with ethyl acetate (240 cc in total). The organic extracts are combined, dried over anhydrous magnesium sulphate, filtered and concentrated to dryness under reduced pressure (20 mm Hg; 2.7 kPa) at a temperature in the region of 45° C. The residue is distilled under reduced pressure. N-Ethyl-N-(3-acetoxypropyl)benzylamine (5.38 g), b.p. 95° C. at 0.2 mm Hg (13.4 Pa), is thereby obtained.

EXAMPLE 12

A solution of N-[3-(α-hydroxyiminobenzyl)phenyl]-3-(3-pyridyl)-1H,3H-pyrrolo[1,2-c]thiazole-7-carboxamide (mixture of E and Z forms) (4 g) in anhydrous N,N-dimethylformamide (40 cc) is added under nitrogen and in the course of 45 minutes at a temperature in the region of 20° C. to a 50% strength suspension (0.62 g) of sodium hydride in liquid paraffin. A solution of N-(2-chloroethyl)morpholine dihydrochloride (1.77 g) in anhydrous N,N-dimethylformamide (40 cc) is added to the solution obtained in the course of 40 minutes at a temperature in the region of 18° C. The suspension obtained is stirred at a temperature in the region of 20° C. for 18 hours. A further portion (0.21 g) of a 50% strength suspension of sodium hydride in liquid paraffin is then added, followed again by N-(2-chloroethyl)morpholine hydrochloride (0.85 g). The suspension obtained is heated to a temperature in the region of 65° C. for 20 hours and then, after cooling to a temperature in the region of 20° C., is treated with distilled water (650 cc) and extracted 3 times with ethyl acetate (300 cc in total). The organic extracts are combined and extracted with 0.1 N aqueous hydrochloric acid solution (100 cc) and the aqueous phase is extracted twice with ethyl ether (100 cc in total). The aqueous phase is brought to a pH in the region of 10 by adding N aqueous sodium hydroxide solution and extracted 3 times with ethyl acetate (300 cc). The organic extracts are combined, washed 3 times with distilled water (150 cc in total), dried over anhydrous magnesium sulphate, filtered and concentrated to dryness under reduced pressure (20 mm Hg; 2.7 kPa) at a temperature in the region of 30° C. A product (5 g) is obtained, which is chromatographed on a column 5 cm in diameter containing silica (0.02–0.045 mm) (600 g). The column is eluted with a mixture of ethyl acetate and methanol (90:10 by volume) at a pressure of 0.5 bar (51 kPa), collecting 500-cc fractions. The first 8 fractions are discarded. The next 32 fractions are combined and concentrated to dryness under reduced pressure (20 mm Hg; 2.7 kPa) at a temperature in the region of 40° C. A product (3 g) is thereby obtained, which is redissolved in ethyl acetate (30 cc). The solution obtained is treated with a 5.6 N solution (1.95 cc) of hydrogen chloride gas in ethyl ether. The crystals which appear are separated by filtration, washed twice with ethyl acetate (10 cc in total) and dried under reduced pressure (20 mm Hg; 2.7 kPa) at a temperature in the region of 20° C. The product obtained (2.8 g) is dissolved in distilled water (30 cc) and the resulting solution is brought to a pH in the region of 10 by adding N aqueous sodium hydroxide solution and extracted 3 times with ethyl acetate (60 cc). The organic extracts are combined, washed twice with distilled water (20 cc in total), dried over anhydrous magnesium sulphate, filtered and concentrated to dryness under reduced pressure (20 mm Hg; 2.7 kPa) at a temperature in the region of 35° C. A product (1.77 g) is thereby obtained. This product is dissolved in 0.13 N aqueous hydrochloric acid solution (23.2 cc) and the solution obtained is lyophilized. N-{3-[α-(2-Morpholinoethoxyimino)benzyl]phenyl}-3-(3-pyridyl)1H,3H-pyrrolo[1,2-c]thiazole-7-carboxamide (mixture of E and Z forms) (1.64 g) is thereby obtained in the form of a cream-coloured lyophilisate.

N-[3-(α-Hydroxyiminobenzyl)phenyl]-3-(3-pyridyl)-1H,3H-pyrrolo[1,2-c]thiazole-7-carboxamide (mixture of E and Z forms) may be obtained in the following manner: hydroxylamine hydrochloride (7.5 g) and sodium carbonate (5.7 g) are added to a solution, heated to a temperature in the region of 70° C., of N-(3-benzoylphenyl)-3-(3-pyridyl)-1H,3H-pyrrolo[1,2-c]thiazole-7-carboxamide (23 g) in 1-propanol (270 cc). The suspension obtained is heated to reflux for 3 hours and stirred at a temperature in the region of 20° C. for 18 hours. The crystals which appear are separated by filtration washed 3 times with distilled water (150 cc in total) and dried under reduced pressure (20 mm Hg; 2.7 kPa) at a temperature in the region of 20° C. N-[3-(α-Hydroxyiminobenzyl)phenyl]-3-(3-pyridyl)-1H,3H-pyrrolo[1,2-c]thiazole-7-carboxamide (mixture of E and Z forms) (8.3 g) is thereby obtained in the form of cream-coloured crystals, m.p. 210° C.

N-(3-Benzoylphenyl)-3-(3-pyridyl)-1H,3H-pyrrolo[1,2-c]thiazole-7-carboxamide may be obtained according to the method described in the European Patent Application published under No. 0,253,711.

EXAMPLE 13

A 50% strength dispersion (0.22 g) of sodium hydride in liquid paraffin is added at room temperature under a stream of nitrogen and with stirring to a solution of (+)-N-[3-(α-hydroxyimino-benzyl)phenyl]-3-(3-pyridyl)-1H,3H-pyrrolo[1,2-c]-thiazole-7-carboxamide (mixture of E and Z forms) (1.63 g) in anhydrous N,N-dimethylformamide (16 cc). A solution of 1-(2-chloroethyl)-4-benzylpiperazine dihydrochloride (0.9 g) in anhydrous N,N-dimethyl-formamide (5 cc) is then added in the course of approximately 5 minutes. The solution is then stirred for 20 hours at room temperature and concentrated to dryness under reduced pressure (20 mm Hg; 2.7 kPa) at a temperature in the region of 40° C. The pasty residue is ground in acetone (40 cc), the sodium chloride formed is separated by filtration and washed with acetone (15 cc in total) and the filtrate is evaporated under reduced pressure (20 mm Hg; 2.7 kPa) at a temperature in the region of 40° C. A pasty orange residue (3.1 g) is thereby obtained. This product is chromatographed on a column 3 cm in diameter containing silica (0.02–0.045 mm) (65 g). The column is eluted with a mixture of ethyl acetate at a pressure of 0.5 bar (51 kPa), collecting 90-cc fractions. The first 15 fractions are discarded; the next 19 fractions are combined and concentrated to dryness under reduced pressure (20 mm Hg; 2.7 kPa) at a temperature in the region of 40° C. A product (1.45 g) is thereby obtained. This product is dissolved in ethyl acetate (5 cc). The solution obtained is treated with ethyl ether (10 cc) and a 4 N solution (2 cc) of hydrogen chloride gas in ethyl ether, then diluted with ethyl ether (20 cc) and stirred at a temperature in the region of 20° C. for 15 minutes. The crystals obtained are separated by filtration, washed 4 times with ethyl ether (40 cc in total) and dried under reduced pressure (0.1 mm Hg; 13.5 Pa) at a temperature in the region of 20° C. (+)-N-[3-{α-[2-(4-Benzyl-1-piperazinyl)ethoxyimino]benzyl}-phenyl-3-(3-pyridyl)-1H,3H-pyrrolo[1,2-c]thiazole-7-carboxamide dihydrochloride (mixture of E and Z forms) (1.5 g) is thereby obtained in the form of white crystals, m.p. 186° C.

(+)-N-[3-(α-Hydroxyiminobenzyl)phenyl]-3-(3-pyridyl)-1H,3H-pyrrolo[1,2-c]thiazole-7-carboxamide is obtained as described in Example 1.

1-Benzyl-4-(2-chloroethyl)piperazine dihydrochloride may be obtained according to the method described by D. C. KRIESEL and O. GRISVOLD, J. Pharm. Sci., 56, 325 (1967).

EXAMPLE 14

Sodium hydride (in 50% strength dispersion in liquid paraffin) (0.68 g) is added at room temperature under a stream of nitrogen and with stirring to a solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (3.0 g) in anhydrous N,N-dimethylformamide (22 cc). After 15 minutes' stirring at room temperature, (2-chloroethyl)methylamine hydrochloride (0.9 g) is added, stirring at room temperature is maintained for 15 hours and the reaction medium is then poured into distilled water (250 cc). After 1 hour's stirring at room temperature, the solid is separated off by filtration, washed with distilled water to neutrality, then dissolved in ethyl acetate 16 cc) and filtered. 4.1 N ethereal hydrogen chloride (1.57 cc) is then added and, after 1 hour's stirring at room temperature, the crystals are separated by filtration, washed with ethyl acetate (6 cc) and diethyl ether (40 cc) and dried under reduced pressure (0.1 mm Hg; 13.5 Pa) at a temperature in the region of 20° C. The hydrochloride obtained (3.04 g) is dissolved in distilled water (30 cc), 1 N sodium hydroxide (6 cc) is added and the mixture is extracted twice with ethyl acetate (40 cc in total). The organic extracts are combined, washed with distilled water (15 cc), dried over anhydrous magnesium sulphate, filtered and concentrated under reduced pressure (20 mm Hg; 2.7 kPa) at a temperature in the region of 40° C. An ochre meringue-like product (2.4 g) is obtained, which is chromatographed on a column 4 cm in diameter containing silica (0.02–0.045 mm) (approximately 150 g). The column is eluted with a mixture of acetonitrile and ammonia solution (d=0.92) (95:5 by volume) at a pressure of 0.5 bar (51 kPa), collecting 80-cc fractions. The first 14 fractions are discarded. The next 3 fractions are combined and concentrated to dryness under reduced pressure (20 mm Hg; 2.7 kPa) at a temperature in the region of 45° C. A product (1.47 g) is thereby obtained. This product is dissolved in ethyl acetate (9 cc) treated with decolorizing charcoal (0.2 g), filtered and treated with 4 N ethereal hydrogen chloride (1.50 cc) and then with diethyl ether (15 cc). The crystals which appear are separated by filtration, washed with diethyl ether (15 cc in total) and dried under reduced pressure (0.1 mm Hg; 13.5 Pa) at a temperature in the region of 40° C. (+)-N-(3-[α-(2-Methylaminoethoxyimino)benzyl]phenyl}-3-(3-pyridyl)1H,3H-pyrrolo[1,2-c]thiazole-7-carboxamide hydrochloride (1.6 g), in the state of a mixture of E and Z forms, is thereby obtained in the form of white crystals, m.p. 150°–155° C.

(+)-N-[3-(α-Hydroxyiminobenzyl)phenyl]-3-(3-pyridyl)-1H,3H-pyrrolo[1,2-c]thiazole-7-carboxamide (mixture of E and Z forms) is obtained as described in Example 1.

EXAMPLE 15

A 1 N ethanolic solution (3.8 cc) of methanesulphonic acid and then 30% strength (110 volumes) hydrogen peroxide (0.2 cc) are added successively to a solution of (+)-N-3-{α-[(1-methyl-4-piperidyloxy)imino]benzyl}phenyl-3-(3-pyridyl)-1H,3H-pyrrolo[1,2-c]thiazole-7-carboxamide (mixture of E and Z forms) (1 g) in 100% strength acetic acid (20 cc); stirring at room temperature is maintained for 15 hours and the solvent is concentrated under reduced pressure (0.1 mm Hg; 13.5 Pa) at a temperature in the region of 30° C. The residue is dissolved in distilled water (25 cc), alkalinized with sodium hydroxide (d=1.33) (8 cc) and diluted with acetone (15 cc) and ethyl acetate (30 cc); the organic phase is separated after settling has taken place and the aqueous phase is extracted with ethyl acetate (30 cc). The organic extracts are combined, washed twice with distilled water (40 cc in total), dried over anhydrous magnesium sulphate and evaporated to dryness under reduced pressure (20 mm Hg; 2.7 kPa) at a temperature in the region of 45° C. A pinkish meringue-like product (814 mg) is thereby obtained This product is chromatographed on a column 3 cm in diameter containing silica (0.02–0.045 mm) (approximately 50 g). The column is eluted with a mixture of acetonitrile and ammonia solution (d=0.92) (95:5 by volume) at a pressure of 0.5 bar (51 kPa), collecting 25-cc fractions. The first 10 fractions are discarded, the next 4 fractions are combined and concentrated to dryness under reduced pressure (20 mm Hg; 2.7 kPa) at a temperature in the region of 40° C. A product (430 mg) is thereby obtained. This product is dissolved in ethyl acetate (3 cc). The solution is treated with decolorizinq charcoal (100 mg) and filtered off. The filter is rinsed with ethyl acetate (1.5 cc in total). The solution obtained is treated with 3.25 N ethereal hydrogen chloride (0.47 cc) and stirred at a temperature in the region of 20° C. for 30 minutes. Diethyl ether (9 cc) is added and stirring is maintained for a further hour at room temperature, and the crystals are then separated by filtration, washed with diethyl ether (10 cc in total) and dried in the air at a temperature in the region of 20° C. (2RS,3R)(+)-N-[3-{α-[(1-Methyl-4-piperidyloxy)imino]benzyl}phenyl]-3-(3-pyridyl)-1H,3H-pyrrolo[1,2-c]thiazole-7-carboxamide 2-oxide dihydrochloride (460 mg) is thereby obtained in the state of a mixture of E and Z forms, m.p. 200° C.

(+)-N-[3-{α-[(1-Methyl-4-piperidyloxy)imino]benzyl}phenyl]-3-(3-pyridyl)-1H,3H-pyrrolo[1,2-c]thiazole-7-carboxamide, in the state of a mixture of E and Z forms, may be prepared as indicated in Example 10.

EXAMPLE 16

A solution of (+)-N-3-{α-[3-(4-tert-butyloxycarbonyl-1-piperazinyl)propoxyimino]benzyl)phenyl-3-(3-pyridyl)-1H,3H-pyrrolo[1,2-c]thiazole-7-carboxamide (mixture of E and Z forms) (4.24 g) in ethyl acetate (100 cc) is stirred in the presence of 3.2 N ethereal hydrogen chloride (8 cc) for 5 hours at room temperature and is then filtered. The solid obtained, washed with diethyl ether (10 cc) and ethyl acetate (15 cc), is then dissolved in 10% strength sodium carbonate solution (50 cc) and extracted 3 times with dichloromethane (150 cc in total). The organic extracts are washed with brine (50 cc) at a concentration of 250 g/l, dried over anhydrous magnesium sulphate and concentrated to dryness under reduced pressure (20 mm Hg; 2.7 kPa). The 3.6 g obtained are suspended in diethyl ether (50 cc), treated with 3 N ethereal hydrogen chloride (25 cc), diluted with ethyl acetate (20 cc) and stirred for 4 hours 30 minutes at room temperature. The crystals which appear are separated by filtration, washed with diethyl ether (20 cc), then dissolved in distilled water (50 cc), alkalinized to pH 9 with 10% strength sodium carbonate solution and extracted with dichloromethane (450 cc in total). The organic phases are dried over anhydrous magnesium sulphate and evaporated to dryness under reduced pressure (20 mm Hg; 2.7 kPa) at a temperature in the region of 40° C. A pinkish meringue-like product (2.7 g) is thereby obtained. This product is chromatographed on a column 1.8 cm in diameter containing neutral alumina (0.032–0.063 mm) (50 g) deactivated with 10% of water. The column is eluted with a mixture of ethyl acetate and methanol (80:20 by volume) at a pressure of 0.5 bar (51 kPa), collecting 20-cc fractions. The first 3 fractions are discarded The next 17 fractions are combined and concentrated to dryness under reduced pressure (20 mm Hg; 2.7 kPa) at a temperature in the region of 40° C. A beige meringue-like product (1.82 g) is thereby obtained, which, with the addition of 0.4 g originating from another operation, is chromatographed a second time on a column 1.4 cm in diameter containing neutral alumina (0.032–0.063 mm) (20 g) deactivated with 10% of water. The column is eluted with ethyl acetate (300 cc), a mixture (180 cc) of ethyl acetate and methanol (95:5 by volume), and a 90:10 mixture (180 cc) and an 80:20 mixture (400 cc) of ethyl acetate and methanol, at a pressure of 0.5 bar (51 kPa), collecting 100-cc fractions. The first fraction is discarded. The next 10 fractions are combined and concentrated to dryness under reduced pressure (20 mm Hg; 2.7 kPa) at a temperature in the region of 40° C. A product (1.7 g) is obtained, which is dissolved in ethyl acetate (20 cc). This solution is treated with 3.05 N ethereal hydrogen chloride (0.7 cc) and stirred at a temperature in the region of 20° C. for 10 minutes. The crystals obtained are separated by filtration, washed with ethyl acetate (10 cc) and diethyl ether (10 cc) and dried under reduced pressure (0.1 mm Hg; 13.5 Pa) at a temperature in the region of 60° C. (+)-N-[3-{α-[3-(1-piperazinyl)propoxyimino]benzyl}phenyl]-3-(3-pyridyl)-1H,3H-pyrrolo[1,2-c]thiazole-7-carboxamide dihydrochloride (0.6 g) is thereby obtained in the state of a mixture of E and Z forms, m.p. 195° C.

(+)-N-[3-{α-[3-(4-tert-Butyloxycarbonyl-1-piperazinyl)propoxyimino]benzyl}phenyl-3-(3-pyridyl)-1H,3H-pyrrolo[1,2-c]thiazole-7-carboxamide (mixture of E and Z forms) may be prepared in the following manner: sodium hydride (in 60% strength dispersion in liquid paraffin) (0.56 g) is added at room temperature under a stream of nitrogen and with stirring to a solution of (+)-N-[3-(α-hydroxyiminobenzyl)-phenyl]-3-(3-pyridyl)1H,3H-pyrrolo[1,2-c]thiazole-7-carboxamide (mixture of E and Z forms) (5.5 g) in anhydrous N,N-dimethylformamide (50 cc). After stirring for 1 hour 25 minutes at room temperature, a solution of 3-(4-tert-butoxycarbonyl-1-piperazinyl)propyl paratoluenesulphonate (6.25 g) in anhydrous N,N-dimethylformamide (25 cc) is introduced in the course of approximately 5 minutes. Stirring is maintained for 19 hours at room temperature and the solvent is evaporated to dryness under reduced pressure (0.1 mm Hg; 13.5 Pa) at a temperature in the region of 45° C. The residue is suspended in ethyl acetate (100 cc) at room temperature; the insoluble matter is separated by filtration and washed with ethyl acetate (40 cc) and the filtrate is evaporated to dryness under reduced pressure (20 mm Hg; 2.7 kPa) at a temperature in the region of 35° C. The residue (13.5 g) is chromatographed on a column 3.5 cm in diameter containing neutral alumina (0.032–0.063 mm) (250 g) deactivated with 10% of water. The column is eluted with a mixture of ethyl acetate and cyclohexane (80:20 by volume) at a pressure of 0.5 bar (51 kPa), collecting 50-cc fractions. The first 2 fractions are discarded. The next 2 fractions are combined and concentrated to dryness under reduced pressure (20 mm Hg; 2.7 kPa) at a temperature in the region of 45° C. A product (7.1 g) is thereby obtained, which is re-chromatographed a second time on a column 2.7 cm in diameter containing neutral alumina (0.032–0.063 mm) (150 g) deactivated with 10% of water. The column is eluted with a mixture of ethyl acetate and cyclohexane (50:50 by volume). The first 4 fractions are discarded. The next 7 fractions are combined and concentrated to dryness under reduced pressure (20 mm Hg; 2.7 kPa) at a temperature in the region of 40° C. (+)-N-3-{α-[3-(4-tert-Butyloxycarbonyl-1-piperazin-yl)propoxyimino]-benzyl}phenyl-3-(3-pyridyl)-1H,3H-pyrrolo[1,2-c]thiazole-7-carboxamide (mixture of E and Z forms) (4.4 g) is thereby obtained in the form of an orange-coloured oil.

3-(4-tert-Butoxycarbonyl-1-piperazinyl)propyl para-toluenesulphonate may be prepared in the following manner: a solution of para-toluenesulphonyl chloride (11.6 g) in pyridine (50 cc) is added in the course of 1 hour 50 minutes to a solution, cooled to 0° C., of 1-(3-hydroxypropyl)-4-tert-butoxycarbonylpiperazine (13.5 g) in pyridine (50 cc), and the mixture is stirred for 15 hours at a temperature in the region of 20° C. The temperature is brought to 10°–15° C. and triethylamine (8.5 cc) is introduced, followed by distilled water (170 cc) and ethyl acetate (170 cc). The organic phase is separated after settling has taken place and the aqueous phase is extracted with ethyl acetate (300 cc in total). The organic extracts are combined, washed with distilled water (750 cc), dried over anhydrous magnesium sulphate, treated with decolorizing charcoal (0.2 g), filtered and evaporated to dryness under reduced pressure (20 mm Hg; 2.7 kPa) at a temperature in the region of 45° C. 3-(4-tert-Butoxycarbonyl-1-piperazinyl)propyl para-toluenesulphonate (16.3 g) is thereby obtained in the form of a red oil.

1-(3-Hydroxypropyl)-4-tert-butoxycarbonylpiperazine may be prepared in the following manner: a solution of di-tert-butyl dicarbonate (12 g) in dichloromethane (100 cc) is treated with a solution of 1-(3-hydroxypropyl)piperazine (7.2 g) in dichloromethane (100 cc); stirring is maintained for 24 hours at room temperature and the solvent is evaporated to dryness under reduced pressure (20 mm Hg; 2.7 kPa) at a temperature in the region of 45° C. 1-(3-Hydroxypropyl)-4-tert-butoxycarbonylpiperazine (13.8 g) is thereby obtained in the form of a yellow oil (Rf=0.25; thin-layer chromatography on silica, eluent: ethyl acetate).

EXAMPLE 17

A solution of (+)-N-(3-benzoylphenyl)-3-(3-pyridyl)-1H,3H-pyrrolo[1,2-c]thiazole-7-carboxamide 2,2-dioxide (0.5 g) and (1-methyl-4-piperidyloxy)amine (0.23 g), in the state of a dihydrochloride, in pyridine (10 cc) is heated to reflux for 4 hours. (1-Methyl-4-piperidyloxy)amine dihydrochloride (0.12 g) is added and refluxing is continued for 1 hour. The mixture is cooled to a temperature in the region of 20° C., the solvent is concentrated under reduced pressure (20 mm Hg; 2.7 kPa) at a temperature in the region of 45° C. and the residue is diluted in distilled water (30 cc) and treated with 1N sodium hydroxide (3.4 cc). The crystals which appear are separated by filtration, washed with distilled water (20 cc in total) and dried under reduced pressure (0.1 mm Hg; 13.5 Pa) at a temperature in the region of 20° C. The beige powder obtained (0.59 g) is dissolved in acetone (4 cc). The solution is filtered and treated with ethyl acetate (2.5 cc) and then with 4.1N ethereal hydrogen chloride (0.49 cc). After 15 minutes, stirring at room temperature, the crystals which appear are separated by filtration, washed with diethyl ether (15 cc in total) and dried under reduced pressure (0.1 mm Hg; 13.5 Pa) at a temperature in the region of 60° C. The dihydrochloride (590 mg) dissolved in distilled water (10 cc) is alkalinized with 1N sodium hydroxide (2 cc) and the crystals are then separated by filtration, washed with distilled water to neutrality and dried under reduced pressure (0.1 mm Hg; 13.5 Pa) at a temperature in the region of 20° C. The solid (416 mg) is dissolved in absolute ethanol (2 cc). The solution is treated with decolorizing charcoal (10 mg) and filtered off. The filter is washed with ethyl acetate (6 cc). The solution is treated with 3.65N ethereal hydrogen chloride (0.36 cc). After 15 hours' stirring at room temperature, the crystals are separated off by filtration, washed with diethyl ether (30 cc in total) and dried in the air. (3RS)-N-(3-[α-(1-Methyl-4-piperidyloxy)iminobenzyl]-phenyl)-3-(3-pyridyl)-1H,3H-pyrrolo[1,2-c]thiazole-7-carboxamide 2,2-dioxide dihydrochloride (470 mg), in the state of a mixture of E and Z forms, is thereby obtained in the form of cream-coloured crystals, m.p. 200° C.

(+)-N-(3-Benzoylphenyl)-3-(3-pyridyl)-1H,3H-pyrrolo[1,2-c]thiazole-7-carboxamide 2,2-dioxide is obtained according to the method described in the European Patent Application published under No. 0,253,711.

(1-Methyl-4-piperidyloxy)amine dihydrochloride may be obtained as described in Example 10.

EXAMPLE 18

Sodium hydride (in 50% strength dispersion in liquid paraffin) (0.18 g) is added at room temperature under a stream of nitrogen and with stirring to a solution of (+)-N-[3-(α-hydroxyimino-4-methoxybenzyl)phenyl]-3-(3-pyridyl)-1H,3H-pyrrolo[1,2-c]thiazole-7-carboxamide (mixture of E and Z forms) (1.74 g) in anhydrous N,N-dimethylformamide (17.5 cc). After 30 minutes' stirring at room temperature, a solution of 1-(3-chloropropyl)-4-methylpiperazine (2.61 g) in anhydrous N,N-dimethylformamide (2 cc) is introduced in the course of approximately 5 minutes, and the solution is then stirred for 15 hours at a temperature in the region of 20° C. The solvent is concentrated under reduced pressure (0.5 mm Hg; 67.5 Pa) at a temperature in the region of 50° C., distilled water (25 cc) is then added and crystallization is primed. After 3 hours' stirring at room temperature, the crystals are separated by filtration, washed with distilled water to neutrality and dried in the air. The solid obtained (2.30 g) is then dissolved in ethyl acetate (40 cc) and 0.1N hydrochloric acid (37 cc) is added. The aqueous phase is separated after settling has taken place, washed with ethyl acetate (20 cc) alkalinized with 1N sodium hydroxide (3.7 cc) and extracted with ethyl acetate (40 cc). The organic extracts are combined, dried over anhydrous magnesium sulphate, treated with decolorizing charcoal (50 mg), filtered and concentrated under reduced pressure (20 mm Hg; 2.7 kPa) at a temperature in the region of 45° C. A pale yellow meringue-like product (1.41 g) is thereby obtained, which is dissolved in ethyl acetate (10 cc)and filtered. The filter is rinsed with ethyl acetate (8 cc in total). The solution is treated with 3 N ethereal hydrogen chloride (1.5 cc). The mixture is stirred at a temperature in the region of 20° C. for 1 hour. The crystals which appear are separated by filtration, washed 3 times with diethyl ether (12 cc in total) and dried under reduced pressure (0.1 mm Hg; 13.5 Pa) at a temperature in the region of 50° C. (+)-N-3-{α-[3-(4-Methyl-1-piperazinyl)propoxyimino]-4-methoxybenzyl}phenyl.-3-(3-pyridyl)-1H,3H-pyrrolo-[1,2-c]thiazole-7-carboxamide dihydrochloride (1.53 g), in the state of a mixture of E and Z forms, is thereby obtained in the form of cream-coloured crystals, m.p. 170° C.

(+)-N-[3-(α-Hydroxyimino-4-methoxybenzyl)-phenyl]-3-(3-pyridyl)-1H,3H-pyrrolo[1,2-c]thiazole-7-carboxamide (mixture of E and Z forms) may be prepared in the following manner: sodium carbonate (425 mg) and hydroxylamine hydrochloride (280 mg) are added to a suspension of (+)-N-[3-(4-methoxybenzoyl)-phenyl]-3-(3-pyridyl)-1H,3H-pyrrolo[1,2-c]thiazole-7-carboxamide (1.82 g) in 1-propanol (22 cc). The suspension is heated to reflux with stirring for 2 hours. The solvent is evaporated off under reduced pressure (20 mm Hg; 2.7 kPa) at a temperature in the region of 50° C.; the residue is diluted in distilled water (25 cc) and crystallization is primed. The crystals are separated by filtration, washed with distilled water to neutrality and dried in the air. (+)-N-[3-(α-Hydroxyimino-4-methoxybenzyl)phenyl]-3-(3-pyridyl)1H,3H-pyrrolo[1,2-c]thiazole-7-carboxamide (mixture of E and Z forms) (1.80 g) is thereby obtained in the form of white crystals, m.p. 235° C.

(+)-N-[3-(4-Methoxybenzoyl)phenyl]-3-(3-pyridyl)-1H,3H-pyrrolo[1,2-c]thiazole-7-carboxamide is prepared according to the method described in the European Patent Application published under No. 0,253,711.

EXAMPLE 19

Sodium hydride (in 60% strength dispersion in liquid paraffin) (9 mg) is added at room temperature under a stream of nitrogen and with stirring to a solution of (+)-N-[3-(α-hydroxyiminobenzyl)-6-chlorophenyl]-3-(3-pyridyl)-1H,3H-pyrrolo[1,2-c]thiazole-7-carboxamide (mixture of E and Z forms) (480 mg) in anhydrous N,N-dimethylformamide (5 cc). After 40 minutes' stirring at room temperature, 4-(2-chloroethyl)morpholine (190 mg) is added and the solution is then stirred for 23 hours at a temperature in the region of 20° C. Sodium hydride (in 60% strength dispersion in liquid paraffin) (23 mg) and 4-(2-chloroethyl)morpholine (43 mg) are added and stirring is continued for 24 hours at a temperature in the region of 20° C. The solvent is concentrated under reduced pressure (0.1 mm Hg; 13.5 Pa) at a temperature in the region of 60° C. Ethyl acetate (15 cc) is added. The sodium chloride is separated by filtration and washed with ethyl acetate (20 cc). After evaporation of the solvent under reduced pressure (20 mm Hg; 2.7 kPa) at a temperature in the region of 40° C., the residue (660 mg) is chromatographed on a column 1.4 cm in diameter containing basic alumina (0.050–0.200 mm) (20 g). The column is eluted with ethyl acetate at a pressure of 0.5 bar (51 kPa), collecting 5-cc fractions. The first 8 fractions are discarded. The next 58 fractions are combined and concentrated to dryness under reduced pressure (20 mm Hg; 2.7 kPa) at a temperature in the region of 40° C. A product (370 mg) is thereby obtained, which is dissolved in ethyl acetate (10 cc) and treated with 3N ethereal hydrogen chloride (0.42 cc). The mixture is stirred at a temperature in the region of 20° C. for 10 minutes and the crystals which appear are separated by filtration, washed with ethyl acetate (5 cc) and diethyl ether (10 cc) and dried under reduced pressure (0.1 mm Hg; 13.5 Pa) at a temperature in the region of 25° C. (+)-N-{3-[α-(2-Morpholinoethoxyimino)benzyl]-6-chlorophenyl}-3-(3-pyridyl)-1H,3H-pyrrolo[1,2-c]thiazole-7-carboxamide dihydrochloride (388 mg), in the state of a mixture of E and Z forms, is thereby obtained in the form of cream-coloured crystals, m.p. 154° C.

(+)-N-[3-(α-Hydroxyiminobenzyl)-6-chlorophenyl]-3-(3-pyridyl)-1H,3H-pyrrolo[1,2-c]thiazole-7-carboxamide (mixture of E and Z forms) may be prepared in the following manner: sodium carbonate (113 mg) and hydroxylamine hydrochloride (150 mg) are added to a suspension of (+)-N-(3-benzoyl-6-chlorophenyl)-3-(3-pyridyl)-1H,3H-pyrrolo[1,2-c]thiazole-7-carboxamide (490 mg) in 1-propanol (5.5 cc). The suspension is heated to reflux with stirring for 2 hours and the solvent is evaporated off under reduced pressure (20 mm Hg; 2.7 kPa) at a temperature in the region of 40° C. The residue is diluted in distilled water (40 cc) and crystallization is primed. The crystals are separated by filtration, washed with distilled water (20 cc) and dried in the air. (+)-N-[3-(α-Hydroxyiminobenzyl)-6-chlorophenyl]-3-(3-pyridyl)-1H,3H-pyrrolo[1,2-c]thiazole-7-carboxamide (mixture of E and Z forms) (490 mg) is thereby obtained in the form of white crystals, m.p. 135° C.

(+)-N-(3-Benzoyl-6-chlorophenyl)-3-(3-pyridyl)1H,3H-pyrrolo[1,2-c]thiazole-7-carboxamide is prepared according to the method described in European Patent Application published under No. 0,253,711.

EXAMPLE 20

Sodium hydride (in 50% strength dispersion in liquid paraffin) (220 mg) is added at room temperature under a stream of nitrogen and with stirring to a solution of (+)-N-{3-[hydroxyimino-(2-pyridyl)methyl]phenyl}-3-(3-pyridyl)-1H,3H-pyrrolo[1,2-c]thiazole-7-carboxamide (mixture of E and Z forms) (2.02 g) in anhydrous N,N-dimethylformamide (20 cc). After 25 minutes' stirring at a temperature in the region of 20° C., a solution of 1-(3-chloropropyl)-4-methylpiperazine (813 mg) in anhydrous N,N-dimethylformamide (2 cc) is introduced in the course of approximately 5 minutes, and the solution is then stirred for 21 hours at room temperature. The solvent is concentrated under reduced pressure (0.5 mm Hg; 67.5 Pa) at a temperature in the region of 50° C., and distilled water (40 cc) and ethyl acetate (40 cc) are then added. The organic phase is separated after settling has taken place and the aqueous phase is extracted with ethyl acetate (40 cc). The organic extracts are combined, dried over anhydrous magnesium sulphate, treated with decolorizing charcoal (50 mg), filtered and concentrated under reduced pressure (20 mm Hg; 2.7 kPa) at a temperature in the region of 45° C. A beige meringue-like product (2.32 g) is thereby obtained, which is dissolved in ethyl acetate (23 cc). The solution is filtered, rinsed with ethyl acetate (8 cc) and treated with 3N ethereal hydrogen chloride (2.6 cc). After 1 hour's stirring at room temperature, the crystals which appear are separated by filtration, washed 3 times with ethyl acetate (12 cc in total) and dried under reduced pressure (0.1 mm Hg; 13.5 Pa) at a temperature in the region of 50° C. The dihydrochloride (2.29 g) is dissolved in distilled water (40 cc) alkalinized with 2N sodium hydroxide (4 cc). After the addition of acetone (30 cc) in order to solubilize, ethyl acetate (40 cc) and distilled water (40 cc) are added. The organic phase is separated after settling has taken place and the aqueous phase is extracted with ethyl acetate (40 cc). The organic extracts are combined, dried over anhydrous magnesium sulphate and evaporated under reduced pressure (20 mm Hg; 2.7 kPa) at a temperature in the region of 45° C. The beige meringue-like product obtained (1.74 g) is dissolved in ethyl acetate (10 cc). The solution is filtered, washed with ethyl acetate (7.5 cc) and treated with 3N ethereal hydrogen chloride (1.87 cc). The crystals which appear are separated by filtration, washed with ethyl acetate (15 cc) and dried under reduced pressure (0.1 mm Hg; 13.5 Pa) at a temperature in the region of 50° C. (+)-N-3-{-[3-(4-Methyl-1-piperazinyl)propoxyimino]-(2-pyridyl)methyl}phenyl]-3-(3-pyridyl)-1H,3H-pyrrolo[1,2-c]thiazole-7-carboxamide (1.65 g), in the state of a mixture of E and Z forms, is obtained in the form of cream-coloured crystals, m.p. 180° C.

(+)-N-{3-[Hydroxyimino-(2-pyridyl)methyl]-phenyl}-3-(3-pyridyl)-1H,3H-pyrrolo[1,2-c]thiazole-7-carboxamide (mixture of E and Z forms) may be prepared in the following manner sodium carbonate (530 mg) and hydroxylamine hydrochloride (350 mg) are added to a suspension of (+)-N-[3-(2-pyridylcarbonyl)-phenyl]-3-(3-pyridyl)-1H,3H-pyrrolo[1,2-c]thiazole-7-carboxamide (2.13 g) in 1-propanol (26 cc). The suspension is heated to reflux with stirring for 1 hour and the solvent is evaporated off under reduced pressure (0.5 mm Hg; 67.5 Pa) at a temperature in the region of 50° C., then the residue is diluted in distilled water (25 cc) and crystallization is primed. After 24 hours' stirring at room temperature, the crystals are separated by filtration, washed with distilled water to neutrality and dried in the air. (+)-N-{3-[Hydroxyimino-(2-pyridyl)methyl]phenyl}-3-(3-pyridyl)-1H,3H-pyrrolo[1,2-c]thiazole-7-carboxamide (mixture of E and Z forms) (2.11 g) is thereby obtained in the form of white crystals, m.p. 150°-160° C.

(+)-N-[3-(2-Pyridylcarbonyl)phenyl]-3-(3-pyridyl)-1H,3H-pyrrolo[1,2-c]thiazole-7-carboxamide is prepared according to the method described in the European Patent Application published under No. 0,253,711.

EXAMPLE 21

A suspension of (+)-N-3-{α-[3-(1-piperazinyl)propoxyimino]benzyl}phenyl-3--(3-pyridyl)-1H,3H-pyrrolo[1,2-c]thiazole-7-carboxamide (mixture of E and Z forms) (1 g), potassium carbonate (134 mg) and 2-bromoethanol (0.134 cc) in acetonitrile (20 cc) is stirred at a temperature in the region of 20° C. for 24 hours. The insoluble matter is separated by filtration and the filtrate is concentrated to dryness under reduced pressure (20 mm Hg; 2.7 kPa) at a temperature in the region of 40° C. A yellow oil (1.13 g) is obtained, which is chromatographed on a column 1.7 cm in diameter containing neutral alumina (0.032–0.063 mm) (50 g) deactivated with 10% of water. The column is eluted with a mixture of ethyl acetate and methanol (80:20 by volume) at a pressure of 0.5 bar (51 kPa), collecting 25-cc fractions. The first 2 fractions are discarded. The next 2 fractions are combined and concentrated to dryness under reduced pressure (2 mm Hg; 2.7 kPa) at a temperature in the region of 40° C. The yellow meringue-like product (800 mg) obtained is chromatographed a second time on a column 1.4 cm in diameter containing neutral alumina (25 g) deactivated with 10% of water (0.032–0.063 mm). The column is eluted with a mixture of ethyl acetate and methanol (90:10 by volume) at a pressure of 0.5 bar (51 kPa), collecting 15-cc fractions. The first 5 fractions are discarded. The next 7 fractions are combined and concentrated to dryness under reduced pressure (20 mm Hg; 2.7 kPa) at a temperature in the region of 40° C. The product obtained (465 mg) is dissolved in ethyl acetate (5 cc) and treated with 3N ethereal hydrogen chloride (0.51 cc). After 15 minutes' stirring at a temperature in the region of 20° C., the crystals which appear are separated by filtration, washed with ethyl acetate (2 cc) and diethyl ether (5 cc) and dried under reduced pressure (0.1 mm Hg; 13.5 Pa) at a temperature in the region of 20° C. (+)-N-{3-[α{3-[4-(2-Hydroxyethyl)-1-piperazinyl]-propoxy-imino}benzyl]phenyl[-3-(3-pyridyl)-1H,3H-pyrrolo-1,2-c]thiazole-7-carboxamide dihydrochloride (460 mg) in the state of a mixture of E and Z forms, is thereby obtained in the form of white crystals, m.p. 178° C.

(+)-N-[3-{α-[3-(1-Piperazinyl)propoxyimino]benzyl}phenyl-3-(3-pyridyl)-1H,3H-pyrrolo[1,2-c]thiazole-7-carboxamide (mixture of E and Z forms) is obtained as described in Example 16.

EXAMPLE 22

A suspension of (+)-N-{3-[α{2-[N-(2-chloroethyl)anilino]ethoxyimino}benzyl-phenyl[-3-(3-pyridyl)-1H,3H-pyrrolo1,2-c]thiazole-7-carboxamide (mixture of E and Z forms) (3.11 g), methylamine hydrochloride (680 mg), potassium carbonate (2.07 g) and cuprous iodide (950 mg) in acetonitrile (62 cc) is heated in an autoclave for 6 hours at 100° C. The insoluble matter is filtered off and rinsed 3 times with acetonitrile (60 cc in total). The filtrate is evaporated to dryness under reduced pressure (20 mm Hg; 2.7 kPa) at a temperature in the region of 45° C. A green gum (1.30 g) is obtained. In a separate vessel, the solid is suspended in ammonia solution (d=0.92) (300 cc), ethyl acetate (300 cc) is added and the organic phase is separated after settling has taken place washed with distilled water (200 cc), dried over anhydrous magnesium sulphate and concentrated to dryness under reduced pressure (20 mm Hg; 2.7 kPa) at a temperature in the region of 45° C. The residue is diluted in ethyl acetate (20 cc); 0.5N hydrochloric acid (20 cc) is added and the aqueous phase is separated after settling has taken place, alkalinized with 5N sodium hydroxide (2.2 cc) and extracted with ethyl acetate (40 cc in total). The organic extracts are combined, dried over anhydrous magnesium sulphate and evaporated to dryness under reduced pressure (20 mm Hg; 2.7 kPa) at a temperature in the region of 40° C. An ochre meringue-like product (1.15 g) is obtained, which, with the addition of the green gum (1.3 g) previously obtained, is chromatographed on a column 3.5 cm in diameter containing silica (0.02–0.045 mm) (approximately 125 g). The column is eluted with a mixture of acetonitrile and ammonia solution (d=0.92) (95:5 by volume) at a pressure of 0.3 bar (30.6 kPa), collecting 80-cc fractions. The first 15, fractions are discarded. The next 3 fractions are combined and concentrated to dryness under reduced pressure (20 mm Hg; 2.7 kPa) at a temperature in the region of 50° C. A yellow meringue-like product (370 mg) is thereby obtained, which is dissolved in ethyl acetate (3.7 cc) and filtered, and the insoluble matter is rinsed with ethyl acetate (1.7 cc). The solution obtained is treated with 3N ethereal hydrogen chloride (0.39 cc) and is stirred at a temperature in the region of 20° C. for 15 minutes. The suspension is diluted with diethyl ether (20 cc) and stirred for 1 hour at a temperature in the region of 20° C., and the crystals are separated by filtration, washed with diethyl ether (20 cc in total) and dried under reduced pressure (0.1 mm Hg; 13.5 Pa) at a temperature in the region of 50° C. (+)-N-{3-[α-{2-[N-(2-Methylaminoethyl)anilino]ethoxyimino}benzyl[phenyl]3-(3-pyridyl)-1H,3H-pyrrolo[1,2-c]thiazole-7-carboxamide dihydrochloride (mixture of E and Z forms) (370 mg) is thereby obtained in the form of yellowish crystals, m.p. 150°-155° C.

(+)-N-{3-[α-{2-[N-2-Chloroethyl)anilino]ethoxyimino}benzylphenyl.}-3-(3-pyridyl)-1H,3H-pyrrolo[1,2-c]thiazole-7-carboxamide (mixture of E and Z forms) may be prepared in the following manner: a solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (4.4 g) in anhydrous N,N-dimethylformamide (10 cc) is added under a stream of nitrogen in the course of approximately 25 minutes to a suspension of sodium hydride (in 50% strength dispersion in liquid paraffin) (480 mg) in anhydrous N,N-dimethylformamide (10 cc). After 15 minutes' stirring at room temperature, a solution of N,N-bis(2-chloroethyl)aniline (2.18 g) in anhydrous N,N-dimethylformamide (10 cc) is introduced in the course of approximately 2 minutes. The solution is then stirred for 16 hours at room temperature. The solvent is concentrated to dryness under reduced pressure (0.1 mm Hg; 13.5 Pa) at a temperature in the region of 45° C. The residue is suspended in distilled water (80 cc). After 1 hour's stirring at a temperature in the region of 20° C., the crystals are separated by filtration, washed with distilled water (20 cc in total) and dried under reduced pressure (0.1 mm Hg; 13.5 Pa) at a temperature in the region of 20° C. A residue (6.32 g) is thereby obtained, which is chromatographed on a column 5.5 cm in diameter containing silica (0.02-0.045 mm) (approximately 250 g). The column is eluted with ethyl acetate at a pressure of 0.5 bar (51 kPa), collecting 100-cc fractions. The first 10 fractions are discarded. The next 8 fractions are combined and concentrated to dryness under reduced pressure (20 mm Hg; 2.7 kPa) at a temperature in the region of 45° C. (+)-N-{3[α-{2-[N-(2-Chloroethyl)anilino]ethoxyimino}benzylphenyl[-3-(3-pyridyl)-1H,3H-pyrrolo[1,2-c]thiazole-7-carboxamide (mixture of E and Z forms) (3.41 g) is thereby obtained in the form of a yellow meringue-like product (Rf=0.54; thin-layer chromatography on silica; eluent: ethyl acetate).

(+)-N-[3-(α-Hydroxyiminobenzyl)phenyl]-3-(3-pyridyl)-1H,3H-pyrrolo[1,2-c]thiazole-7-carboxamide (mixture of E and Z forms) is obtained as described in Example 1.

EXAMPLE 23

Sodium hydride (in 60% strength dispersion in liquid paraffin) (0.42 g) is added at room temperature under a stream of nitrogen and with stirring to a solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (4.18 g) in anhydrous N,N-dimethylformamide (40 cc). The suspension is stirred for 1 hour at a temperature in the region of 20° C. and a solution of (3RS)-3-quinuclidinyl para-toluenesulphonate (3.27 g) in anhydrous N,N-dimethylformamide (25 cc) is then introduced in the course of approximately 5 minutes. The solution is stirred for 18 hours at room temperature and then heated to 70° C. for 6 hours. After the temperature has been brought back to about 20° C., the solvent is evaporated off under reduced pressure (0.1 mm Hg; 13.5 Pa) at a temperature in the region of 40° C. The residue is diluted in ethyl acetate (40 cc); the soluble matter is filtered off and washed with ethyl acetate (20 cc) and the filtrate is evaporated to dryness under reduced pressure (20 mm Hg; 2.7 kPa) at a temperature in the region of 40° C. A pasty red residue (7.5 g) is thereby obtained. This product is chromatographed on a column 2.4 cm in diameter containing neutral alumina (0.050-0.200 mm) (150 g). The column is eluted with a mixture of ethyl acetate and methanol (90:10 by volume), collecting 100-cc fractions. The first 12 fractions are discarded. The next 4 fractions are combined and concentrated to dryness under reduced pressure (20 mm Hg; 2.7 kPa) at a temperature in the region of 40° C. The product obtained (3.34 g) is chromatographed a second time on a column 1.9 cm in diameter containing alumina (0.050-0.200 mm) (60 g). The column is eluted with ethyl acetate (1000 cc) and a mixture (1000 cc) of ethyl acetate and methanol (90:10 by volume), collecting 100-cc fractions. The first 10 fractions are discarded. The next 10 fractions are combined and concentrated to dryness under reduced pressure (20 mm Hg; 2.7 kPa) at a temperature in the region of 40° C. An orange-coloured meringue-like product (0.97 g) is thereby obtained, which is chromatographed on a column 3 cm in diameter containing silica (0.02-0.045 mm) (65 g). The column is eluted with a mixture of ethyl acetate and diethylamine (95:5 by volume) at a pressure of 0.5 bar (51 kPa), collecting 40-cc fractions. The first 21 fractions are discarded. The next 19 fractions are combined and concentrated to dryness under reduced pressure (20 mm Hg; 2.7 kPa) at a temperature in the region of 40° C. A product (0.64 g) is thereby obtained. This product is dissolved in ethyl acetate (10 cc) and treated with 3N ethereal hydrogen chloride (0.81 cc). After 10 minutes, stirring at room temperature, the crystals which appear are separated by filtration, washed with ethyl acetate (20 cc) and diethyl ether (20 cc in total) and dried under reduced pressure (0.1 mm Hg; 13.5 Pa) at a temperature in the region of 50° C. (+)-N-[3-{α-[((3RS)-3-Quinuclidinyl)oxyimino]benzyl}phenyl-3-(3-pyridyl)-1H,3H-pyrrolo[1,2-c]thiazole-7-carboxamide dihydrochloride (mixture of E and Z forms) (0.64 g) is thereby obtained in the form of a beige powder, m.p. 200° C.

(+)-N-[3-(α-Hydroxyiminobenzyl)phenyl]-3-(3-pyridyl)-1H,3H-pyrrolo[1,2-c]thiazole-7-carboxamide is obtained as described in Example 1.

(3RS)-3-Quinuclidinyl para-toluenesulphonate may be obtained in the following manner: para-toluenesulphonyl chloride (6.3 g), dissolved in pyridine (15 cc), is added under a stream of nitrogen and with stirring in the course of approximately 1 hour 30 minutes to a solution, cooled to 0° C., of (3RS)-3-quinuclidinol (3.8 g) in pyridine (15 cc), and the mixture is stirred for 2 hours at between 5 and 10° C. and then 12 hours at a temperature in the region of 20° C. The temperature is brought back to 15° C. and triethylamine (4.63 cc) is added. The reaction medium is poured into distilled water (100 cc). Ethyl acetate (100 cc) is added; the aqueous phase is separated after settling has taken place and washed with ethyl acetate (200 cc in total). The organic extracts are combined, washed twice with distilled water (200 cc in total), dried over anhydrous magnesium sulphate and evaporated to dryness under reduced pressure (20 mm Hg; 2.7 kPa) at a temperature in the region of 35° C. (3RS)-3-Quinuclidinyl para-toluenesulphonate (6.5 g) is thereby obtained in the form of a red oil, which is used as it is.

EXAMPLE 24

Sodium hydride (in 50% strength dispersion in liquid paraffin) (220 mg) is added at a temperature in the region of 20° C. under a stream of nitrogen and with stirring to a solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (2.0 g) in anhydrous N,N-dimethylformamide (10 cc). The suspension is stirred for 30 minutes at a temperature in the region of 20° C. and cooled to 0° C., and a solution of (3RS)-1-methyl-3-piperidyl paratoluenesulphonate (1.2 g) in anhydrous N,N-dimethylformamide (6 cc) is introduced in the course of approximately 30 minutes. The solution, stirred for 2 hours at 0° C. and then 16 hours at room temperature, is thereafter poured into distilled water (100 cc). The suspension is extracted 3 times with ethyl acetate (150 cc in total) and washed twice with distilled water (100 cc in total). The organic phase is acidified with 0.1N hydrochloric acid (50 cc) and the aqueous phase is separated after settling has taken place and neutralized with 5N sodium hydroxide (1.2 cc). It is extracted twice with ethyl acetate (50 cc), the organic phase is treated with decolorizing charcoal (100 mg) and dried over anhydrous magnesium sulphate and the solvent is evaporated off under reduced pressure (20 mm Hg; 2.7 kPa) at a temperature in the region of 45° C. An ochre meringue-like product (1.6 g) is obtained, which is chromatographed on a column 3.5 cm in diameter containing silica (0.020–0.045 mm) (125 g). The column is eluted with a mixture of acetonitrile and ammonia solution (d=0.92) (97:3 by volume) at a pressure of 0.3 bar (21 kPa), collecting 80-cc fractions. The first 20 fractions are discarded. The next 7 fractions are combined and concentrated to dryness under reduced pressure (20 mm Hg; 2.7 kPa) at a temperature in the region of 45° C. A pale yellow meringue-like product (1.6 g) is thereby obtained. This product is dissolved in ethyl acetate (6.6 cc) and the solution is filtered, treated with 3N ethereal hydrogen chloride (1.4 cc) and diluted with diethyl ether (20 cc). After 30 minutes' stirring at room temperature, the crystals which appear are separated by filtration, washed with diethyl ether (20 cc in total) and dried under reduced pressure (0.1 mm Hg; 13.5 Pa) at a temperature in the region of 50° C. (3R)-(+)-N-[3-{α-[((3RS)-1-Methyl-3-piperidyloxy)imino]benzyl}-phenyl]-3-(3-pyridyl)-1H,3H-pyrrolo[1,2-c]thiazole-7-carboxamide (mixture of E and Z forms) (1.3 g) is thereby obtained in the form of a yellow powder, m.p. 165°–170° C.

(+)-N-[3-(α-Hydroxyiminobenzyl)phenyl]-3-(3-pyridyl)-1H,3H-pyrrolo[1,2-c]thiazole-7-carboxamide is obtained as described in Example 1.

(3RS)-1-Methyl-3-piperidyl para-toluenesulphonate may be obtained in the following manner: a solution of para-toluenesulphonyl chloride (9.5 g) in pyridine (25 cc) is added with stirring in the course of approximately 30 minutes to a solution of (3RS)-1-methyl-3-piperidinol (5.8 g) in pyridine (25 cc), and the mixture is stirred for 2 hours a between 5 and 10° C. and then 12 hours at a temperature in the region of 20° C. Triethylamine (7.1 cc) is added while the temperature is maintained at about 20° C. The reaction medium is poured into distilled water (150 cc). Ethyl acetate (150 cc) is added; the aqueous phase is separated after settling has taken place and washed with ethyl acetate (100 cc in total). The organic extracts are combined, washed twice with distilled water (80 cc in total), dried over anhydrous magnesium sulphate and evaporated to dryness under reduced pressure (20 mm Hg; 2.7 kPa) at a temperature in the region of 45° C. (3RS)-1-Methyl-3-piperidyl paratoluenesulphonate (8.8 g) is thereby obtained in the form of a red oil [Rf=0.72; thin-layer chromatography on silica; eluent: acetonitrile/ammonia solution (d=0.92) (95:5 by volume)].

EXAMPLE 25

Sodium hydride (in 50% strength dispersion in liquid paraffin) (0.29 g) is added at room temperature under a stream of nitrogen and with stirring to a solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (2.2 g) in anhydrous N,N-dimethylformamide (20 cc). After 45 minutes' stirring at room temperature, a solution of N,N-diethylchloroacetamide (0.75 g) in anhydrous N,N-dimethylformamide (5 cc) is introduced in the course of approximately 1 minute, stirring at room temperature being maintained for 15 hours, and the solvent is then concentrated to dryness under reduced pressure (0.1 mm Hg; 13.5 Pa) at a temperature in the region of 60° C. The residue is diluted in acetone (30 cc) and the insoluble matter is filtered off and washed twice with acetone (20 cc in total). The filtrate is evaporated to dryness under reduced pressure (20 mm Hg; 2.7 kPa) at a temperature in the region of 40° C. An orange-coloured product (3.4 g) is obtained, which is chromatographed on a column 3 cm in diameter containing silica (0.02–0.045 mm) (approximately 150 mg). The column is eluted with ethyl acetate at a pressure of 0.5 bar (51 kPa), collecting 30-cc fractions. The first 18 fractions are discarded. The next 13 fractions are combined and concentrated to dryness under reduced pressure (20 mm Hg; 2.7 kPa) at a temperature in the region of 45° C. The product obtained (2.15 g) is dissolved in acetonitrile (6 cc) and is treated with 4N ethereal hydrogen chloride (2.9 cc). After 15 minutes' stirring at room temperature, the crystals which appear are separated by filtration, washed twice with diethyl ether (20 cc in total) and dried under reduced pressure (0.1 mm Hg; 13.5 Pa) at a temperature in the region of 20° C. (+)-N-{3-[α-(Diethylcarbamoylmethoxyimino)benzyl]phenyl{-3-(3-pyridyl)-1H,3H-pyrrolo[1,2-c]thiazole-7-carboxamide dihydrochloride (2 g), in the state of a mixture of E and Z forms, is thereby obtained in the form of white crystals, m.p. 135° C.

(+)-N-[3-(α-Hydroxyiminobenzyl)phenyl]-3-(3-pyridyl)-1H,3H-pyrrolo[1,2-c]thiazole-7-carboxamide (mixture of E and Z forms) is obtained as described in Example 1.

EXAMPLE 26

Sodium hydride (in 60% strength dispersion in liquid paraffin) (0.5 g) is added at room temperature under a stream of nitrogen and with stirring to a solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (2.2 g) in anhydrous N,N-dimethylformamide (20 cc). The suspension is stirred for 1 hour at room temperature and 4-(2-chloroethyl)-morpholine hydrochloride (0.72 g) is then added. After 15 hours' stirring at room temperature, the solvent is evaporated to dryness under reduced pressure (0.1 mm Hg; 13.5 Pa) at a temperature in the region of 45° C. A pasty orange residue (3.8 g) is thereby obtained. This product is chromatographed on a column 3 cm in diameter containing silica (0.02-0.045 mm) (approximately 65 g). The column is eluted with ethyl acetate at a pressure of 0.5 bar (51 kPa), collecting 50-cc fractions. The first 7 fractions are discarded. The next 43 fractions are combined and concentrated to dryness under reduced pressure (20 mm Hg; 2.7 kPa) at a temperature in the region of 40° C. The residue (1.8 g) is chromatographed a second time on a column 3 cm in diameter containing silica (0.02-0.045 mm) (65 g). The column is eluted with ethyl acetate at a pressure of 0.5 bar (51 kPa), collecting 150-cc fractions. The first 15 fractions are discarded. The next 21 fractions are combined and concentrated to dryness under reduced pressure (20 mm Hg; 2.7 kPa) at a temperature in the region of 40° C. The meringue-like product obtained (1.4 g) is dissolved in ethyl acetate (40 cc) and 4N ethereal hydrogen chloride (2 cc) is added. The crystals which appear are separated by filtration, washed successively with ethyl acetate (15 cc) and with diethyl ether (20 cc) and dried under reduced pressure (0.1 mm Hg; 13.5 Pa) at a temperature in the region of 60° C. The white residue obtained (1.4 g) is dissolved in distilled water (10 cc). After the addition of 10% strength sodium carbonate solution (10 cc), the solution is extracted 3 times with ethyl acetate (50 cc in total). The organic extracts are combined, washed with distilled water (40 cc), dried over anhydrous magnesium sulphate, treated with decolorizing charcoal (0.2 9), filtered and concentrated under reduced pressure (20 mm Hg; 2.7 kPa) at a temperature in the region of 35° C. A pale yellow meringue-like product (0.5 g) is thereby obtained, which is chromatographed on a column 1.7 cm in diameter containing neutral alumina (30 g) deactivated with 10% of water (0.032-0.063 mm). The column is eluted with ethyl acetate (200 cc) and a 95:5 (by volume) mixture (210 cc) of ethyl acetate and methanol at a pressure of 0.5 bar (51 kPa), collecting 10-cc fractions. The first 21 fractions are discarded. The next 25 fractions are combined and concentrated to dryness under reduced pressure (20 mm Hg; 2.7 kPa) at a temperature in the region of 40° C. The residue (0.55 g) is dissolved in ethyl acetate (2 cc). The solution obtained is treated with 3.9N ethereal hydrogen chloride (0.58 cc), ethyl acetate (2 cc) and diethyl ether (5 cc). After 5 minutes' stirring at a temperature in the region of 20° C., the crystals obtained are separated by filtration, washed with ethyl acetate (2 cc) and diethyl ether (5 cc) and dried under reduced pressure (0.1 mm Hg; 13.5 Pa) at a temperature in the region of 60° C. (+)-N-{3-[α-(2-Morpholinoethoxyimino)benzyl]phenyl}-3-(3-pyridyl)-1H,3H-pyrrolo[1,2-c]thiazole-7-carboxamide (0.58 g), in the state of a mixture of E and Z forms, is thereby obtained in the form of a dihydrochloride, m.p. 163° C.

(+)-N-[3-(α-Hydroxyiminobenzyl)phenyl]-3-(3-pyridyl)-1H,3H-pyrrolo[1,2-c]thiazole-7-carboxamide is obtained as described in Example 1.

EXAMPLE 27

Sodium hydride (in 50% strength dispersion in liquid paraffin) (0.12 g) is added at room temperature under a stream of nitrogen and with stirring to a solution of (+)-N-[3-(α-hydroxyiminobenzyl)phenyl]-3-(3-pyridyl)-1H,3H-pyrrolo[1,2-c]thiazole-7-carboxamide (mixture of E and Z forms) (1 g) in anhydrous N,N-dimethylformamide (7.4 cc). A solution of 1-methyl-4-piperidyl para-toluenesulphonate (0.67 g) in anhydrous N,N-dimethylformamide (6.7 cc) is then introduced in the course of approximately 5 minutes. The solution is stirred for 15 hours at room temperature, a further portion (0.14 g) of 1-methyl-4-piperidyl paratoluenesulphonate is then added and stirring is continued for a further 3 hours. This operation is repeated 3 times and the reaction medium is diluted with distilled water (100 cc). After 15 minutes' stirring at room temperature, the solid is separated by filtration and washed twice with distilled water (40 cc in total). The residue is dissolved in ethyl acetate (50 cc) and 0.1N hydrochloric acid (46 cc) is added. The aqueous phase is separated after settling has taken place and alkalinized with sodium hydroxide (d=1.33) (5 cc). After 2 hours' stirring at room temperature, the crystals are separated by filtration and washed with distilled water (20 cc in total). (+)-N-[3-{° -[(1-Methyl-4-piperidyl)oxyimino]benzyl}phenyl]-3-(3-pyridyl)-1H,3H-pyrrolo[1,2-c]thiazole-7-carboxamide (mixture of E and Z forms) (0.82 g) is thereby obtained in the form of a cream-coloured powder [Rf=0.33; thin-layer chromatography; eluent: acetonitrile/ammonia solution (d=0.92) (95:5 by volume)].

(+)-N-[3-(α-Hydroxyiminobenzyl)phenyl]-3-(3-pyridyl)-1H,3H-pyrrolo[1,2-c]thiazole-7-carboxamide is obtained as described in Example 1.

1-Methyl-4-piperidyl para-toluenesulphonate may be obtained in the following manner: para-toluenesulphonyl chloride (19.60 g) is added in the course of approximately 1 hour 30 minutes to a solution, cooled to 0° C., of 4-hydroxy-1-methylpiperidine (11.50 g) in pyridine (50 cc), and the mixture is stirred for 4 hours at 0° C. and then 12 hours at a temperature in the region of 20° C. After the addition of triethylamine (14.10 g) and stirring for a further 15 minutes, distilled water (300 cc) and ethyl acetate (300 cc) are added. The aqueous phase is separated after settling has taken place and washed with ethyl acetate (200 cc). The organic extracts are combined, washed with distilled water (500 cc in total), dried over anhydrous magnesium sulphate and evaporated to dryness under reduced pressure (20 mm Hg; 2.7 kPa) at a temperature in the region of 45° C. The final traces of pyridine are removed under a higher vacuum (0.1 mm Hg; 13.5 Pa). 1-Methyl-4-piperidyl para-toluenesulphonate (19.6 g) is thereby obtained in the form of a brown oil [Rf=0.56; thin-layer chromatography on silica; eluent: acetonitrile/ammonia solution (d=0.92) (95:5 by volume)].

EXAMPLE 28

7-Chloroformyl-3-(3-pyridyl)-1H,3H-pyrrolo[1,2-c]thiazole hydrochloride (3.3 g) and then triethylamine (2.3 cc) are added successively in the course of approximately 5 minutes to a solution of (Z){O-[3-(4-methyl-1-piperazinyl)propyl]-3-aminobenzophenone oxime} (3.5 g) in dichloromethane (45 cc), and the mixture is stirred at room temperature for 12 hours. After the addition of further portions of 7-chloroformyl-3-(3-pyridyl)-1H,3H-pyrrolo[1,2-c]thiazole hydrochloride (0.6 g) and triethylamine (0.6 g), the solution is stirred again for 1 hour and the solvent is evaporated to dryness under reduced pressure (20 mm Hg; 2.7 kPa) at a temperature in the region of 35° C. The residue is then treated with distilled water (50 cc) and with ethyl acetate (50 cc). The organic phase is separated after settling has taken place, washed with distilled water (35 cc in total), dried over anhydrous magnesium sulphate and concentrated under reduced pressure (20 mm Hg; 2.7 kPa) at a temperature in the region of 40° C. The residue (6.6 g) is chromatographed on a column 6 cm in diameter containing silica (0.063-0.200 mm) (approximately 400 g), using the following elution gradient: a 99:1 (by volume) mixture (280 cc) of acetonitrile and ammonia solution (d=0.92); this fraction is discarded; and a 95:5 mixture (350 cc) and a 90:10 mixture (280 cc) of acetonitrile and ammonia solution. The latter 2 fractions are combined and concentrated to dryness under reduced pressure (20 mm Hg; 2.7 kPa) at a temperature in the region of 50° C. The cream-coloured meringue-like product obtained (4.6 g) is dissolved in ethyl acetate (60 cc). The solution is treated with decolorizing charcoal (0.5 g), filtered and treated with 3.25N ethereal hydrogen chloride (4.8 cc). After 30 minutes' stirring at room temperature, the crystals which appear are separated by filtration, washed with ethyl acetate (100 cc in total) and dried under reduced pressure (0.1 mm Hg; 13.5 Pa) at a temperature in the region of 50° C. (+)-N-3-{α-[3-(4-Methyl-1-piperazinyl)propoxyimino]benzyl}phenyl-3-(3-pyridyl)-1H,3H-pyrrolo[1,2-c]thiazole-7-carboxamide dihydrochloride form B (4.8 g), m.p. 168° C., is thereby obtained.

7-Chloroformyl-3-(3-pyridyl)-1H,3H-pyrrolo[1,2-c]thiazole hydrochloride is prepared according to the method described in European Patent No. 115,979.

(Z)-{O-[3-(4-Methyl-1-piperazinyl)propyl]-3-aminobenzophenone oxime} may be prepared in the following manner: a solution of (Z)-(3-aminobenzophenone oxime) (5 g) in anhydrous N,N-dimethylformamide (35 cc) is added in the course of approximately 15 minutes to a suspension of sodium hydride (in 50% strength dispersion in liquid paraffin) (1.14 g) in anhydrous N,N-dimethylformamide (35 cc). The medium is stirred for 15 minutes at room temperature and a solution of 1-(3-chloropropyl)-4-methylpiperazine (4.17 g) in anhydrous N,N-dimethylformamide (35 cc) is introduced in the course of 5 minutes at a temperature in the region of 2° C. After 12 hours' stirring at room temperature, the solvent is evaporated to dryness under reduced pressure (0.1 mm Hg; 13.5 Pa) at a temperature in the region of 50° C. The residue is diluted in ethyl acetate (50 cc), the inorganic salts are filtered off and washed with ethyl acetate (50 cc in total) and the filtrates are concentrated to dryness under reduced pressure (20 mm Hg; 2.7 kPa) at a temperature in the region of 45° C. (Z)-{O-[3-(4-Methyl-1-piperazinyl)propyl]-3-aminobenzophenone oxime} (9.2 g) is thereby obtained in the form of an orange-coloured oil [Rf=0.23; thin-layer chromatography on silica; eluent: ethyl acetate/diethylamine (95:5 by volume)].

(Z)-(3-Aminobenzophenone oxime) may be prepared in the following manner: a pyridine solution (600 cc) of 3-aminobenzophenone (32 g) and hydroxylamine hydrochloride (22.6 g) is heated to reflux for 4 hours and the solvent is then evaporated off under reduced pressure (20 mm Hg; 2.7 kPa) at a temperature in the region of 50° C. The residue is then diluted with distilled water (400 cc) and crystallization is primed. After 2 hours' stirring at room temperature, the crystals are separated by filtration and washed with distilled water (1 liter in total) 3-Aminobenzophenone oxime (mixture of E and Z forms) (35.4 g) is thereby obtained in the form of a beige powder. 3 fractions (11.8 each) were chromatographed on a column 7 cm in diameter containing silica (0.02-0.045 mm) (600 g) with a mixture of methylene chloride and ethyl acetate (80:20 by volume) at a pressure of 0.5 bar (51 kPa) and collecting 100-cc fractions. The first 19 fractions are discarded. The next 8 fractions corresponding to the Z form are combined, the next 13, a mixture of E and Z forms, are discarded and the final 26 are combined to form a batch enriched in E form. The two batches are concentrated to dryness under reduced pressure (20 mm Hg; 2.7 kPa) at a temperature in the region of 40° C. 11.2 and 9.5 g ar Ⓡobtained, respectively. The two products are each resuspended in diisopropyl ether (50 cc) and the crystals are separated by filtration, washed with diisopropyl ether (20 cc in total) and dried under reduced pressure (20 mm Hg; 2.7 kPa) at a temperature in the region of 20° C. (Z)-(3-Aminobenzophenone oxime) (10.43 g), and a mixture (5.7 g) 80% enriched in (E)-(3-aminobenzophenone oxime) which will be used as it is, are thereby obtained.

EXAMPLE 29

7-Chloroformyl-3-(3-pyridyl)-1H,3H-pyrrolo[1,2-c]thiazole hydrochloride (3.5 g) and then triethylamine (3.0 cc) are added successively in the course of approximately 5 minutes to a solution of O-[3-(4-methyl-1-piperazinyl)propyl]-3-aminobenzophenone oxime E form (80% pure) (2.9 g in dichloromethane (30 cc), and the mixture is stirred at room temperature for 1 hour 30 minutes. After the addition of a further portion (0.25 g) of 7-chloroformyl-3-(3-pyridyl)-1H,3H-pyrrolo[1,2-c]thiazole hydrochloride, the solution is stirred again for 2 hours 15 minutes and then diluted with distilled water (30 cc). The organic phase is separated after settling has taken place, washed with distilled water (60 cc in total), dried over anhydrous magnesium sulphate and concentrated under reduced pressure (20 mm Hg; 2.7 kPa). The beige meringue-like product (4.1 g) obtained is chromatographed on a column 6 cm in diameter containing silica (0.02-0.045 mm) (approximately 400 g). The column is eluted with a mixture of ethyl acetate and diethylamine (95:5 by volume) at a pressure of 0.5 bar (51 kPa), collecting 100-cc fractions. The first 25 fractions are discarded. The next 30 fractions are combined and concentrated to dryness under reduced pressure (20 mm Hg; 2.7 kPa) at a temperature in the region of 40° C. A meringue-like product (2.9 g) is obtained, which is suspended in ethyl acetate (120 cc) and heated to reflux until dissolution is complete, then cooled to about 25° C. 3.25 M ethereal hydrogen chloride (3.0 cc) is added to this solution and the mixture is stirred at a temperature in the region of 5° C. for 30 minutes. The crystals obtained are separated by filtration, washed with ethyl acetate (25 cc) and diethyl ether (50 cc) and dried under reduced pressure (0.1 mm Hg; 13.5 Pa) at a temperature in the region of 50° C. (+)-N-3-(α-[3-(4-Methyl-1-piperazinyl)propoxyimino]benzyl}phenyl-3-(3-pyridyl)-1H,3H-pyrrolo[1,2-c]thiazole-7-carboxamide dihydrochloride form A (2.6 g), m.p. 160° C., is thereby obtained.

7-Chloroformyl-3-(3-pyridyl)-1H,3H-pyrrolo[1,2-c]thiazole hydrochloride is prepared according to the method described in European Patent No. 0,115,979.

(E)-{O-[3-(4-Methyl-1-piperazinyl)propyl]-3-aminobenzophenone oxime} may be prepared in the following manner: sodium hydride (in 60% strength dispersion in liquid paraffin) (0.7 g) is added at room temperature under a stream of nitrogen and with stirring to a solution of (E)-(3-aminobenzophenone oxime) (3.2 g) in anhydrous N,N-dimethylformamide (20 cc). The mixture is stirred for 1 hour and a solution of 1-(3-chloropropyl)-4-methylpiperazine (2.7 g) in anhydrous N,N-dimethyl-formamide (20 cc) is then introduced in the course of approximately 15 minutes. After stirring for 1 hour 15 minutes at room temperature, the solvent is evaporated to dryness under reduced pressure (0.1 mm Hg; 13.5 Pa) at a temperature in the region of 50° C. The residue is taken up with ethyl acetate (50 cc); the inorganic salts are removed by filtration and washed with ethyl acetate (50 cc) and the solvent is evaporated to dryness under reduced pressure (20 mm Hg; 2.7 kPa) at a temperature in the region of 35° C. The residue is diluted in ethyl acetate (40 cc) and extracted 3 times with 1N hydrochloric acid (40 cc in total), the aqueous phases are then combined and brought to pH 8 with 2N sodium hydroxide and the solution is extracted twice with ethyl acetate (50 cc in total). The organic extracts are combined, dried over anhydrous magnesium sulphate, filtered and concentrated under reduced pressure (20 mm Hg; 2.7 kPa) at a temperature in the region of 40° C. The orange oil (4.5 g) obtained is chromatographed on a column 6 cm in diameter containing silica (0.02–0.045 mm) (approximately 500 g). The column is eluted with a mixture of ethyl acetate and diethylamine (95:5 by volume) at a pressure of 0.5 bar (51 kPa), collecting 80-cc fractions. The first 16 fractions are discarded. The next 16 fractions are combined and concentrated to dryness under reduced pressure (20 mm Hg; 2.7 kPa) at a temperature in the region of 40° C. (E)-{O-[3-(4-Methyl-1-piperazinyl)propyl]-3-aminobenzophenone oxime} (3.8 g) is thereby obtained in the form of an orange-coloured oil [Rf=0.32, thin-layer chromatography on silica; eluent: ethyl acetate/diethylamine (95:5 by volume)].

3-Aminobenzophenone oxime 80% enriched in the E form is obtained as described above.

EXAMPLE 30

(+)-N-[3-{α-[(1-Methyl-4-piperidyloxy)imino]-benzyl}phenyl]-3-(3-pyridyl)-1H,3H-pyrrolo[1,2-c]thiazole-7-carboxamide (1 g) in the state of a mixture of E and Z forms, is chromatographed on a column 4 cm in diameter containing silica (0.02–0.045 mm) (approximately 100 g). The column is eluted with a mixture of diethyl ether and diethylamine (85:15 by volume) at a pressure of 0.2 bar (20 kPa), collecting 25-cc fractions. The first 20 fractions are discarded. The next 11 fractions corresponding to the first oxime form eluted, referred to as form A, are combined, as well as the next 15 fractions corresponding to a mixture 70% enriched in the second oxime form referred to as form B. After evaporation of the solvent under reduced pressure (20 mm Hg; 2.7 kPa) at a temperature in the region of 40° C., form A (0.4 g) and a mixture (0.6 g) enriched in form B are obtained.

EXAMPLE 31

Form A (0.4 g) is dissolved in absolute ethanol (1 cc), filtered and then treated successively with 0.4N ethereal hydrogen chloride (0.9 cc), ethyl acetate (3 cc), 0.4N ethereal hydrogen chloride (0.9 cc) and diethyl ether (5 cc). After 3 hours' stirring at room temperature, the crystals which appear are separated by filtration and dried under reduced pressure (0.1 mm Hg; 13.5 Pa) at a temperature in the region of 20° C. (+)-N-[3-{α-[(1-Methyl-4-piperidyloxy)imino]benzyl}phenyl-3-(3-pyridyl)-1H,3H-pyrrolo[1,2-c]thiazole-7-carboxamide dihydrochloride form A (0.18 g), m.p. 175°–180° C., is obtained.

EXAMPLE 32

The product 70% enriched in form B (0.6 g) is chromatographed a second time on a column 4 cm in diameter containing silica (0.02–0.045 mm) (approximately 150 g). The column is eluted with a mixture of diethyl ether and diethylamine 85:15 by volume) at a pressure of 0.2 bar (20 kPa), collecting 25-cc fractions. The first 20 fractions are discarded. The next 18 fractions are combined and concentrated to dryness under reduced pressure (20 mm Hg; 2.7 kPa) at a temperature in the region of 40° C. Pure form B (0.39 g) is thereby obtained, which is dissolved in absolute ethanol (2 cc), treated with decolorizing charcoal (0.1 g), filtered and treated with absolute ethanol (2 cc) and with ethyl acetate (10 cc). 4N ethereal hydrogen chloride (0.18 cc) is then added with stirring and, after 1 hour at room temperature, the crystals are separated by filtration and dried under reduced pressure (0.1 mm Hg; 13.5 Pa) at a temperature in the region of 20° C. (+)-N-[3-(α-[(1-Methyl-4-piperidyloxy)imino]benzyl}phenyl]-3-(3-pyridyl)-1H,3H-pyrrolo[1,2c]thiazole-7-carboxamide monohydrochloride form B (0.31 g), m.p. 264° C., is obtained.

EXAMPLE 33

(+)-N-[3-{α-[(1-Methyl-4-piperidyloxy)imino]benzyl}phenyl]-3-(3-pyridyl)-1H,3H-pyrrolo[1,2-c]thiazole-7-carboxamide (mixture of E and Z forms) (11.8 g) is dissolved in absolute ethanol (55 cc) and 3.65 M ethereal hydrogen chloride (6 cc) is added. After 2 hours' stirring at room temperature, the crystals are separated by filtration and dried under reduced pressure (0.1 mm Hg; 13.5 Pa) at a temperature in the region of 20° C. A monohydrochloride (8.0 g) of a product 85% enriched in form B is obtained. The filtrate is concentrated to dryness under reduced pressure (20 mm Hg; 2.7 kPa) at a temperature in the region of 40° C. A brown oil (4.9 g) 90% enriched in form A is obtained.

The solid (form B preponderant) is suspended in absolute ethanol (100 cc) and heated to reflux for 5 minutes, and the temperature is then brought to 20° C. The crystals are separated by filtration and dried under reduced pressure (0.1 mm Hg; 13.5 Pa) at a temperature in the region of 20° C. A monohydrochloride (6.6 g) of the pure form B is obtained. The filtrate, evaporated to dryness under reduced pressure (20 mm Hg; 2.7 kPa) at a temperature in the region of 40° C., yields a yellow meringue-like product (3.7 g) which will be used in the preparation of the oxime of form A. The monohydrochloride (6.6 g) of pure form B is then treated with acetone (25 cc) and thereafter with 1N sodium hydroxide (14 cc) and is extracted with ethyl acetate (50 cc in total). The organic extracts are washed with distilled water to neutrality, dried over anhydrous magnesium sulphate and concentrated to dryness under reduced pressure (20 mm Hg; 2.7 kPa) at a temperature in the region of 40° C. A white meringue-like product (6.2 g) is obtained. To the product (4 g) dissolved in acetonitrile (140 cc), 1 M ethanolic sulphuric acid (7.4 cc) is added. After 15 minutes' stirring at room temperature, the crystals which appear are separated by filtration, washed with acetonitrile (20 cc) and diethyl ether (40 cc) and dried under reduced pressure (0.1 mm Hg; 13.5 Pa) at a temperature in the region of 20° C. (+)-N-[3-{α-[(1-Methyl-4-piperidyloxy)imino]benzyl}phenyl-[3-(3-pyridyl)-1H,3H-pyrrolo[1,2-c]thiazole-7-carboxamide form B (3.5 g) is thereby obtained in the form of an acid sulphate, m.p. 145° C.

In a separate vessel, the oil obtained (90% form A) (4.9 g) is taken up with acetone (35 cc) and treated with 1N sodium hydroxide (20 cc). The aqueous phase is extracted twice with ethyl acetate (100 cc in total). The organic extracts are combined, washed with distilled water to neutrality, dried over anhydrous magnesium sulphate, filtered and concentrated under reduced pressure (20 mm Hg; 2.7 kPa) at a temperature in the region of 45° C. A pasty orange residue (4.85 g) is thereby obtained. This product is chromatographed on a column 6 cm in diameter containing silica (0.02–0.045 mm) (approximately 500 g). The column is eluted with a mixture of diethyl ether and diethylamine (85:15 by volume) at a pressure of 0.5 bar (51 kPa), collecting 100-cc fractions. The first 33 fractions are discarded. The next 19 fractions, composed of pure form A, are combined into a single batch; the final 17, enriched in form A, form a second batch. The solvent is evaporated to dryness under reduced pressure (20 mm Hg; 2.7 kPa) at a temperature in the region of 40° C. Pure form A (2.0 g) and 1.5 g in which A is preponderant are thereby obtained.

These portions (1.5 g and 3.7 g) of meringue-like product obtained above during the purification of form B are combined and chromatographed on a 4-cm column containing silica (0.043–0.063 mm) (150 g). The column is eluted with a mixture of diethyl ether and diethylamine (88:12 by volume) at a pressure of 0.5 bar (51 kPa), collecting 100-cc fractions. The first 46 fractions are discarded. The next 20 fractions are combined and concentrated to dryness under reduced pressure (20 mm Hg; 2.7 kPa) at a temperature in the region of 40° C. Pure form A (2.5 g) is thereby obtained.

This batch and the 2 g already obtained are dissolved in ethyl acetate (40 cc) and treated with decolorizing charcoal (0.2 g). After filtration, the solution is treated with 3.65N ethereal hydrogen chloride (4.1 cc) and is stirred at a temperature in the region of 20° C. for 15 minutes. The crystals are separated by filtration, washed successively with ethyl acetate (20 cc) and diethyl ether (20 cc in total) and dried under reduced pressure (0.1 mm Hg; 13.5 Pa) at a temperature in the region of 20° C. (+)-N-[3-{α-[(1-Methyl-4-piperidyloxy)imino]benzyl}phenyl-3-(3-pyridyl)-1H,3H-pyrrolo[1,2-c]thiazole-7-carboxamide form A (4.1 g) is thereby obtained in the form of a dihydrochloride, m.p. 166° C.

EXAMPLE 34

7-Chloroformyl-3-(3-pyridyl)-1H,3H-pyrrolo[1,2-c]thiazole hydrochloride (4.8 g) and triethylamine (4.5 cc) are added with stirring to a solution of (Z)-[O-(1-methyl-4-piperidyl)-3-aminobenzophenone oxime](4.1 g) in dichloromethane (50 cc). The suspension is stirred for 15 hours at room temperature and a further portion (0.48 g) of 7-chloroformyl-3-(3-pyridyl)-1H,3H-pyrrolo[1,2-c]thiazole hydrochloride is then added. After 1 hour's stirring, distilled water (50 cc) is added and the organic phase is separated after settling has taken place and washed with distilled water (100 cc in total). The organic extracts are dried over anhydrous magnesium sulphate, treated in the presence of decolorizing charcoal, filtered and concentrated under reduced pressure (20 mm Hg; 2.7 kPa) at a temperature in the region of 45° C. A pasty orange residue (6.8 g) is thereby obtained. This product is chromatographed on a column 6 cm in diameter containing silica (0.02–0.045 mm) (approximately 450 g). The column is eluted with a mixture of ethyl acetate and diethylamine (95:5 by volume) at a pressure of 0.5 bar (51 kPa), collecting 100-cc fractions. The first 16 fractions are discarded. The next 24 fractions are combined and concentrated to dryness under reduced pressure (20 mm Hg; 2.7 kPa) at a temperature in the region of 40° C. A product (4.4 g) is thereby obtained in the form of a beige meringue-like material which, with the addition of 1.7 g originating from another operation, is chromatographed a second time on a column 2.7 cm in diameter containing silica (0.02–0.045 mm) (approximately 80 g). The column is eluted with a mixture of ethyl acetate and diethylamine (95:5 by volume) at a pressure of 0.5 bar (51 kPa), collecting 30-cc fractions. The first 15 fractions are discarded. The next 35 fractions are combined and concentrated to dryness under reduced pressure (20 mm Hg; 2.7 kPa) at a temperature in the region of 40° C. A beige meringue-like product (5.5 g) is thereby obtained, which is dissolved in acetonitrile (120 cc), and 1 M ethanolic sulphuric acid (10.2 cc) is added. After 1 hours' stirring at room temperature, the crystals which appear are separated by filtration, washed with ethyl ether (50 cc) and dried under reduced pressure (0.1 mm Hg; 13.5 Pa) at a temperature in the region of 20° C. (+)-N-[3-{α-[(1-Methyl-4-piperidyloxy)imino]benzyl}phenyl]-3-(3-pyridyl)-1H,3H-pyrrolo[1,2-c]thiazole-7-carboxamide form B (5.9 g) is obtained in the form of an acid sulphate, m.p. 153° C.

(Z)-[O-(1-Methyl-4-piperidyl)-3-aminobenzophenone oxime]may be prepared in the following manner: sodium hydride (in 60% strength dispersion in liquid paraffin) (0.72 g) is added at room temperature under a stream of nitrogen and with stirring to a solution of (Z)-(3-aminobenzophenone oxime) (3.48 g) in anhydrous N,N-dimethylformamide (30 cc). The suspension is stirred at room temperature for 45 minutes and a solution of 1-methyl-4-piperidyl para-toluenesulphonate (5.4 g) in anhydrous N,N-dimethylformamide (50 cc) is then introduced in the course of approximately 15 minutes. The solution is then stirred for 1 hour 20 minutes at room temperature and thereafter portions (0.2, 0.3 and 0.6 g) of 1-methyl-4-piperidyl paratoluenesulphonate are added at intervals of 1, 15 and 4 hours, respectively. Sodium hydride (in 60% strength dispersion in liquid paraffin) (0.14 g) and a solution of 1-methyl-4-piperidyl para-toluenesulphonate (1.8 g) in anhydrous N,N-dimethylformamide (5 cc) are then added. The solution is stirred for 15 hours at room temperature, distilled water (300 cc) is then added and the solution is extracted 4 times with ethyl acetate (400 cc in total). The organic extracts are combined, washed with distilled water (500 cc), dried over anhydrous magnesium sulphonate, filtered and concentrated under reduced pressure (20 mm Hg; 2.7 kPa) at a temperature in the region of 45° C. A pasty orange residue (6.8 g) is thereby obtained. This product is chromatographed on a column 6 cm in diameter containing silica (0.02–0.045 mm) (approximately 500 g). The column is eluted with a mixture of ethyl acetate and diethylamine (95:5 by volume) at a pressure of 0.5 bar (51 kPa), collecting 80-cc fractions. The first 15 fractions are discarded. The next 25 fractions are combined and concentrated to dryness under reduced pressure (20 mm Hg; 2.7 kPa) at a temperature in the region of 40° C. (Z)-[0-(1-Methyl-4-piperidyl)-3-aminobenzophenone oxime](4.13 g) is thereby obtained in the form of a yellow oil.

(Z)-(3-Aminobenzophenone oxime) may be prepared as in Example 28.

1-Methyl-4-piperidyl para-toluenesulphonate may be prepared as described in Example 27.

The present invention also relates to medicinal products consisting of a product of general formula (I), in free form or in the form of an addition salt with a pharmaceutically acceptable acid, in the pure state or in the form of a composition in which it is combined with any other pharmaceutically compatible product which can be inert or physiologically active. The medicinal products according to the invention may be used orally, parenterally, rectally or topically.

As solid compositions for oral administration, tablets, pills, powders (in particular in gelatin capsules or wafer capsules) or granules may be used. In these compositions, the active product according to the invention is mixed with one or more inert diluents such as starch, cellulose, sucrose, lactose or silica. These compositions can also comprise substances other than diluents, e.g. one or more lubricants such as magnesium stearate or talc, a colouring, a coating (dragees) or a varnish.

As liquid compositions for oral administration, solutions, suspensions, emulsions, syrups and elixirs of a pharmaceutically acceptable nature, containing inert diluents such as water, ethanol, glycerol, vegetable oils or liquid paraffin, may be used. These compositions can also comprise substances other than diluents, e.g. wetting products, sweeteners, thickeners, flavourings or stabilizers.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, e.g. ethyl oleate or any other suitable organic solvent may be employed.

These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in a sterile injectable medium.

The compositions for rectal administration are suppositories or rectal capsules which contain, apart from the active product, excipients such as cocoa butter, semi-synthetic glycerides or polyethylene glycols.

The compositions for topical administration can be, e.g. creams, ointments, lotions, eye washes, mouth washes, nasal drops or aerosols.

In human therapy, the products according to the invention are especially useful in the treatment of all pathological conditions in which PAF-acether may be directly or indirectly implicated, in particular allergic and inflammatory conditions and conditions of the digestive system such as ulcers, colitis and intestinal lesions caused by irradiation or endotoxin shock.

The dosages depend on the effect sought and the treatment period. They are generally between 25 and 300 mg per day administered orally, intravenously or by inhalation for an adult in one or more doses. Generally speaking, the doctor will determine the dosage he considers most appropriate in accordance with the age, weight and any other factor characteristic of the subject to be treated.

Of very special importance are the products of the general formula (I) in which R represents a hydrogen or halogen atom or an alkyloxy radical in which the alkyl portion contains 1 to 4 carbon atoms, Ar represents a phenyl or pyridyl radical, p is equal to 0, 1 or 2 and:

A—either Z represents a valency bond and $R_2$ represents a hydrogen atom,

B—or Z represents a valency bond and $R_2$ represents a quinuclidinyl or 3- or 4-piperidyl radical in which the nitrogen atom is optionally substituted with an alkyl radical containing 1 to 4 carbon atoms, C—or Z represents an alkylene radical containing 1 to 4 carbon atoms and $R_2$ represents a 2-, 3- or 4-piperidyl radical in which the nitrogen atom is optionally substituted with an alkyl radical containing 1 to 4 carbon atoms, or alternatively $R_2$ represents a radical

in which $R_3$ represents a hydrogen atom or an alkyl radical containing 1 to 4 carbon atoms or a phenyl radical and $R_4$ represents a radical

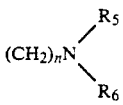

in which n is an integer between 1 and 4 inclusive and $R_5$ and $R_2$, which may be identical or different, represent a hydrogen atom or an alkyl radical containing 1 to 4 carbon atoms, or alternatively $R_2$ represents a radical

in which $R_5$ and $R_6$, which may be identical or different, represent an alkyl radical containing 1 to 4 carbon atoms or a phenylalkyl radical in which the alkyl portion contains 1 to 4 carbon atoms, or alternatively $R_5$ and $R_6$, together with the nitrogen atom to which they are attached, form a morpholine, piperidine or piperazine ring in which the second nitrogen atom can be optionally substituted with an alkyl radical containing 1 to 4 carbon atoms, a hydroxyalkyl radical in which the alkyl portion contains 1 to 4 carbon atoms or a phenylalkyl radical in which the alkyl portion contains 1 to 4 carbon atoms, their enantiomers, their diastereoisomers and their E and Z isomers taken alone or mixed, as well their pharmaceutically acceptable salts.

Of still more special importance are the following products:

(+)-N-[3-{α-[3-(1-Methyl-1-piperazinyl)propoxyimino]benzyl}phenyl-3-(3-pyridyl)-1H,3H-pyrrolo[1,2-c]thiazole-7-carboxamide, mixture of E and Z forms;

(+)-N-{3-[α-(2-dimethylaminoethoxyimino)benzyl]-phenyl}-3-(3-pyridyl)-1H,3H-pyrrolo[1,2-c]thiazole-7-carboxamide, mixture of E and Z forms;

(+)-N-{3-[α-(2-morpholinooxyimino)benzyl]-phenyl)-3-(3-pyridyl)-1H,3H-pyrrolo[1,2-c]thiazole-7-carboxamide, mixture of E and Z forms;

(+)-N-[3-{α-[2-(4-methyl-1-piperazinyl)ethoxyimino]benzyl}phenyl-3-(3-pyridyl)-1H,3H-pyrrolo[1,2-c]thiazole-7-carboxamide, mixture of E and Z forms;

(+)-N-[3-{α-[(1-methyl-4-piperidyloxy)imino]benzyl}phenyl]-3-(3-pyridyl)-1H,3H-pyrrolo[1,2-c]thiazole-7-carboxamide, mixture of E and Z forms;

(+)-N-[3-{α-[3-(4-methyl-1-piperazinyl)propoxyimino]benzyl}phenyl]-3-(3-pyridyl)-1H,3H-pyrrolo[1,2-c]thiazole-7-carboxamide, form A;

(+)-N-[3-{α-[(1-methyl-4-piperidyloxy)imino]benzyl}phenyl]-3-(3-pyridyl)-1H,3H-pyrrolo1,2-c]thiazole-7-carboxamide, form B;

(+)-N-[3-{α-[(1-methyl-4-piperidyloxy)imino]benzyl}phenyl]-3-(3-pyridyl)-1H,3H-pyrrolo[1,2-c]thiazole-7-carboxamide, mixture of E and Z forms;

(2RS,3R)-(+)-N-[3-{α-[(1-methyl-4-piperidyloxy)imino]benzyl}phenyl]-3-(3-pyridyl)-1H,3H-pyrrolo[1,2-c]thiazole-7-carboxamide, 2-oxide, mixture of E and Z forms;

(+)-N-[3-{α-[3-(1-piperazinyl)propoxyimino]benzyl} phenyl]-3-(3-pyridyl)-1H,3H-pyrrolo[1,2-c]thiazole-7-carboxamide, mixture of E and Z forms;

(+)-N-{3-[α-{3-[4-(2-hydroxyethyl)-1-piperazinyl]-propoxyimino}benzyl]phenyl}-3-(3-pyridyl)-1H,3H-pyrrolo[1,2-c]thiazole-7-carboxamide, mixture of E and Z forms; and (3R)-(+)-N-[3-{α-[((3RS)-1-methyl-3-piperidyloxy)imino]benzyl}phenyl]-3-(3-pyridyl)-1H,3H-pyrrolo[1,2-c]thiazole-7-carboxamide, mixture of E and Z forms.

The example which follows, given without implied limitation, illustrates the composition according to the invention.

EXAMPLE A

Injectable unit doses containing 25 mg of active product are prepared according to the usual technique by dissolving (+)-N-{3-[α-(2-morpholinoethoxyimino)-benzyl] phenyl}-3-(3-pyridyl)-1H,3H-pyrrolo[1,2-c]thiazole-7-carboxamide dimethanesulphonate (mixture of E and Z forms) (366.79 mg) in distilled water (25 cc) and distributing the solution obtained equally into 10 identical ampoules.

What is claimed is:

1. A new 1H,3H-pyrrolo[1,2-c]thiazole-7-carboxamide derivative, which is of the general formula:

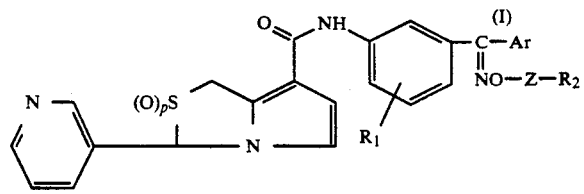

in which $R_1$ represents a hydrogen or halogen atom or an alkyl, alkyloxy, trifluoromethyl, amino, alkylamino, dialkylamino, hydroxy, cyano, phenyl or phenoxy radical, Ar represents a phenyl, naphthyl, pyridyl, quinolyl, isoquinolyl, thienyl, thieno[2,3-b]thien-2-yl or thieno[3,2-b]thien-2-yl, it being possible for these radicals optionally to bear one or more substituents selected from halogen atoms or alkyl, alkyloxy, trifluoromethyl, amino, alkylamino, dialkylamino, hydroxy or cyano radicals, p represents an integer equal to zero, one or two, and A—either Z represents a valency bond and $R_2$ represents a hydrogen atom, B—or Z represents a valency bond and $R_2$ represents a 2-or 4-pyridyl, 3-quinuclidinyl, 3-pyrrolidinyl or 3- or 4-piperidyl radical, it being possible for the latter two radicals to be optionally substituted on the nitrogen atom with an alkyl, hydroxyalkyl, phenyl or phenylalkyl radical, C—or Z represents an alkylene radical containing 1 to 4 carbon atoms and $R_2$ represents a 2-, 3- or 4-pyridyl, 3-quinuclidinyl, 2- or 3-pyrrolidinyl or 2-, 3- or 4-piperidyl radical, it being possible for the latter two radicals to be substituted on the nitrogen atom with an alkyl, hydroxyalkyl, phenyl or phenylalkyl radical, or alternatively $R_2$ represents a radical of general formula:

in which:

a) either $R_3$ and $R_4$, together with the nitrogen atom to which they are attached, form a piperazine ring optionally substituted on the second nitrogen atom with an alkyl, hydroxyalkyl, pyridyl, phenyl or phenylalkyl radical, b) or $R_3$ represents a hydrogen atom or an alkyl, phenyl or phenylalkyl radical or a radical of general formula:

in which n represents an integer between 1 and 4 and $R_5$ and $R_6$, which may be identical or different, represent a hydrogen atom or an alkyl, phenyl or phenylalkyl radical, or alternatively $R_3$ and $R_2$, together with the nitrogen atom to which they are attached, form a morpholine, thiomorpholine, pyrrolidine, piperidine or piperazine ring in which the second nitrogen atom can be optionally substituted with an alkyl, hydroxyalkyl, pyridyl, phenyl, phenylalkyl or phenylcarbonyl radical, and $R_4$ represents a radical of general formula (III) defined as above, on the understanding that the definitions of n, $R_5$ and $R_6$ in the symbols $R_3$ and $R_4$ can be identical or different, D—or Z represents an alkylene radical containing 1 to 4 carbon atoms and $R_2$ represents a radical of general formula:

 (IV)

or

 (V)

in which $R_3$, $R_4$, $R_5$ and $R_6$ are defined as above in C b), on the understanding that the alkyl radicals and alkyl portions contain 1 to 4 carbon atoms in a straight or branched chain and that the invention relates to the racemic products, the enantiomers due to the presence of an asymmetric carbon at the 3-position of the pyrrolothiazole ring, the mixtures of these enantiomers, the diastereoisomers, pure or mixed, due to the possible presence of another chiral centre, and the E and Z (also known as syn and anti) isomers and mixtures thereof originating from the presence of the oxime group C=NO-Z-$R_2$, as well as to the pharmaceutically acceptable salts of the products of formula (I) thus defined.

2. A pharmaceutical composition, which contains at least one derivative according to claim 1, in combination with one or more compatible and pharmaceutically acceptable adjuvants or diluents.

* * * * *